US008512296B2

(12) United States Patent  
Gabriel et al.

(10) Patent No.: US 8,512,296 B2  
(45) Date of Patent: Aug. 20, 2013

(54) INJECTION DEVICE

(75) Inventors: Jochen Gabriel, Stuttgart (DE);  
Joachim Keitel, Esslingen (DE)

(73) Assignee: Haselmeier GmbH, St. Gallen (CH)

( * ) Notice: Subject to any disclaimer, the term of this patent is extended or adjusted under 35 U.S.C. 154(b) by 487 days.

(21) Appl. No.: 12/601,743

(22) PCT Filed: Nov. 5, 2007

(86) PCT No.: PCT/EP2007/009552  
§ 371 (c)(1),  
(2), (4) Date: Nov. 24, 2009

(87) PCT Pub. No.: WO2008/145171  
PCT Pub. Date: Dec. 4, 2008

(65) Prior Publication Data  
US 2010/0168677 A1    Jul. 1, 2010

(30) Foreign Application Priority Data  
May 25, 2007   (DE) .......................... 10 2007 026 083

(51) Int. Cl.  
*A61M 5/00*   (2006.01)

(52) U.S. Cl.  
USPC ............ 604/207; 604/208; 604/209; 604/211

(58) Field of Classification Search  
USPC .......................... 604/181, 186, 189, 207, 211  
See application file for complete search history.

(56) References Cited

U.S. PATENT DOCUMENTS

| 5,674,204 | A |   | 10/1997 | Chanoch | 604/211 |
| 6,004,297 | A |   | 12/1999 | Steenfeldt-Jensen | 604/207 |
| 6,086,567 | A | * | 7/2000 | Kirchhofer et al. | 604/211 |
| 6,221,053 | B1 |   | 4/2001 | Walters et al. | 604/211 |
| 6,235,004 | B1 |   | 5/2001 | Steenfeldt-Jensen et al. | 604/207 |
| 7,309,327 | B2 |   | 12/2007 | Kirchhofer et al. | 604/207 |
| 7,377,912 | B2 |   | 5/2008 | Graf et al. | 604/208 |
| 7,935,088 | B2 | * | 5/2011 | Veasey et al. | 604/207 |
| 8,197,450 | B2 | * | 6/2012 | Glejbol et al. | 604/211 |
| 2004/0186441 | A1 |   | 9/2004 | Graf et al. | 604/207 |
| 2005/0065477 | A1 | * | 3/2005 | Jost | 604/207 |
| 2009/0254047 | A1 |   | 10/2009 | Thogersen et al. | 604/211 |
| 2012/0157932 | A1 | * | 6/2012 | Glejbol et al. | 604/211 |

FOREIGN PATENT DOCUMENTS

| DE | 203 17 377 U | 4/2005 |
| EP | 0 937 471 A | 8/1999 |
| EP | 2047878 A1 | 4/2009 |

(Continued)

*Primary Examiner* — Kevin C Sirmons  
*Assistant Examiner* — Bradley G Thomas, Jr.  
(74) *Attorney, Agent, or Firm* — Milton Oliver, Esq.; Oliver Intellectual Property LLC

(57) ABSTRACT

An injection device (30) features a housing (42, 52) for reception of a container (34) having a fluid (32) to be injected, a first element (94) for ejecting injection fluid (32) from such a container (34), and said first element (94) has an external thread (92). A metering element (66, 88) has an internal thread (90) that is in engagement with the external thread (92) of the first element (94), and said metering element (66) is rotatable, together with the first element (94), for preselection of a desired injection dose. A coupling arrangement (K1) serves, during an injection operation, to create a nonrotatable connection between the first element (94) and the housing (42, 52) and thereby to block, during an injection operation, a rotation of the first element (94) relative to the housing (42, 52) but to enable a rotation of the metering element (66, 88) relative to the housing (42, 52).

20 Claims, 25 Drawing Sheets

(56) References Cited

FOREIGN PATENT DOCUMENTS

| | | |
|---|---|---|
| EP | 1827538 B1 | 8/2009 |
| JP | H11-512332 A | 10/1999 |
| JP | 03-824650 B | 9/2006 |
| WO | WO 97-10865 | 3/1997 |
| WO | WO 97-17095 | 5/1997 |
| WO | WO 99-38554 A | 8/1999 |
| WO | WO 02-53214 | 7/2002 |
| WO | WO 03/011373 A1 | 2/2003 |
| WO | WO 03/011374 A1 | 2/2003 |
| WO | WO 2006-058833 A2 | 6/2006 |
| WO | WO 2006-084876 | 8/2006 |

* cited by examiner

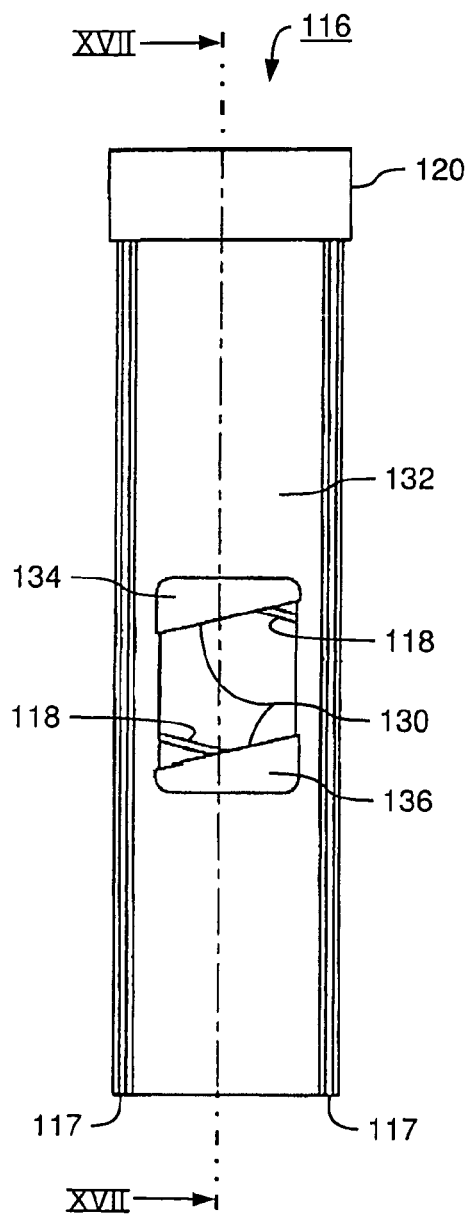
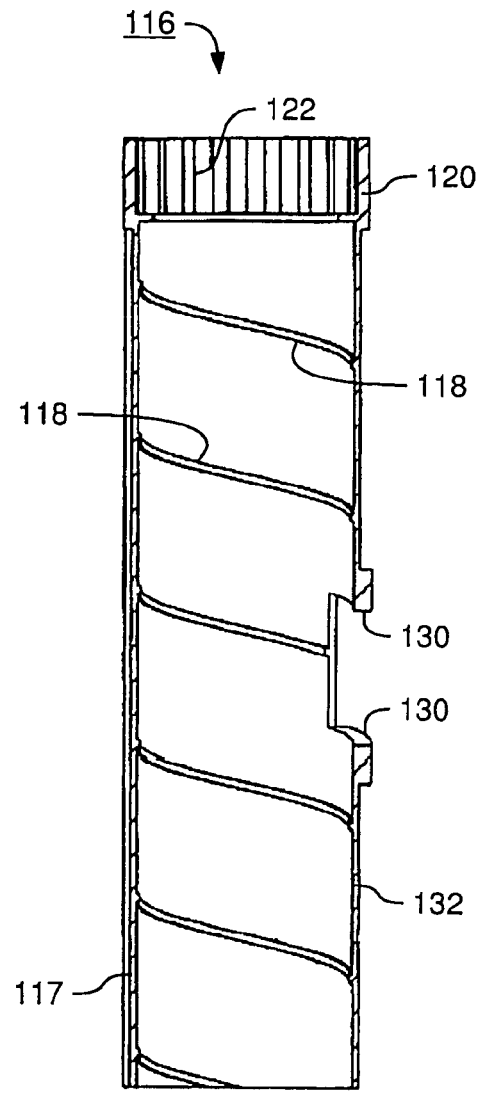
*FIG. 16*  *FIG. 17*

INJECTION DEVICE

CROSS-REFERENCE TO RELATED APPLICATION(S)

This application is a section 371 of PCT/EP07/09552 filed 5 Nov. 2007, published 4 Dec. 2008 as WO-2008-145171-A1, which in turn claims priority from DE 10 2007 026 083.2 filed 25 May 2007, the contents of which are hereby incorporated by reference.

FIELD OF THE INVENTION

The invention relates to an injection device having an injection dose settable by the patient. Such injection devices must be operable in easy and self-evident fashion.

SUMMARY OF THE INVENTION

It is therefore an object of the invention to make available a novel injection device.

This object is achieved by providing a housing, a first element, formed with an external thread, for ejection of fluid from a replaceable container, a metering element formed with an internal thread adapted to engage with the external thread of the first element and which is rotatable with respect to the housing for setting an injection dose, and a coupling arrangement configured to block, during an injection operation, a rotation of the first element with respect to the housing but to enable a rotation of the metering element with respect to the housing, the rotation of the metering element, during an injection operation, permitting an axial displacement of the first element in a patient-proximal direction. In such an injection device, the patient can set the desired injection dose in easy and simple fashion. Such a device also has a simple configuration, which facilitates assembly thereof; its operation is also self-evident, which improves user compliance since brief instructions are sufficient to teach operation.

BRIEF FIGURE DESCRIPTION

Further details and advantageous refinements of the invention are evident from the exemplifying embodiments, in no way to be understood as a limitation of the invention, that are described below and depicted in the drawings.

Figure 1:
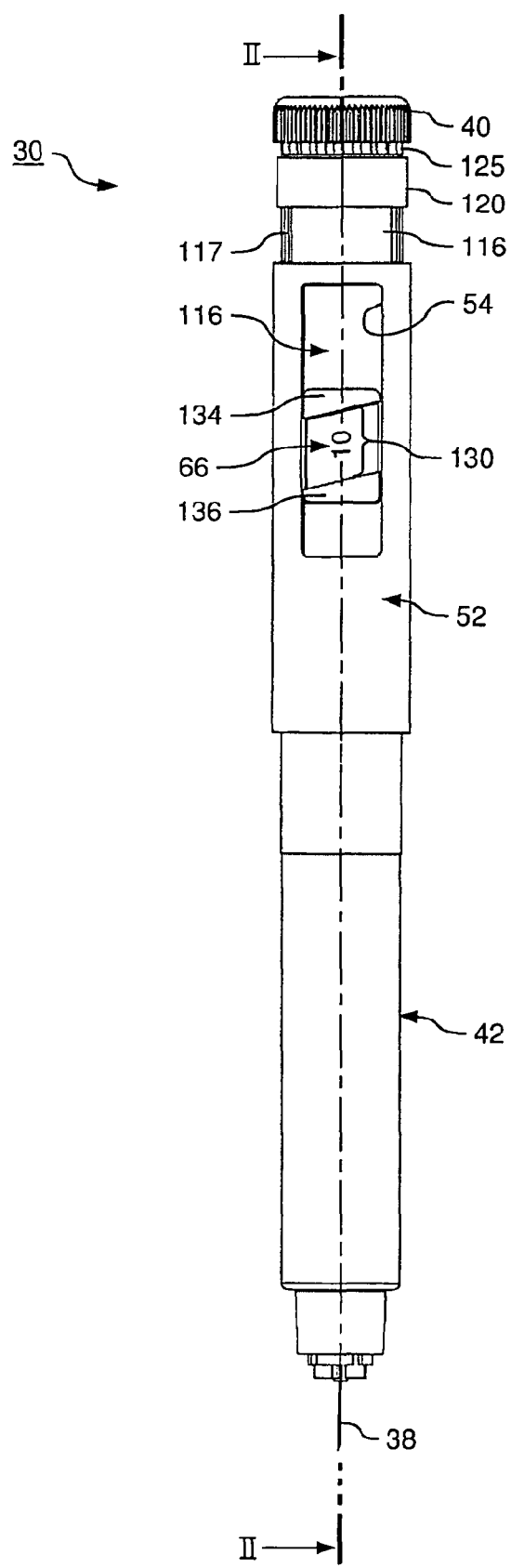
FIG. 1 is a side view of an embodiment of an injection device 30 according to the present invention, prior to an injection, in a state in which an injection dose of 10 units is set.
Figure 2:
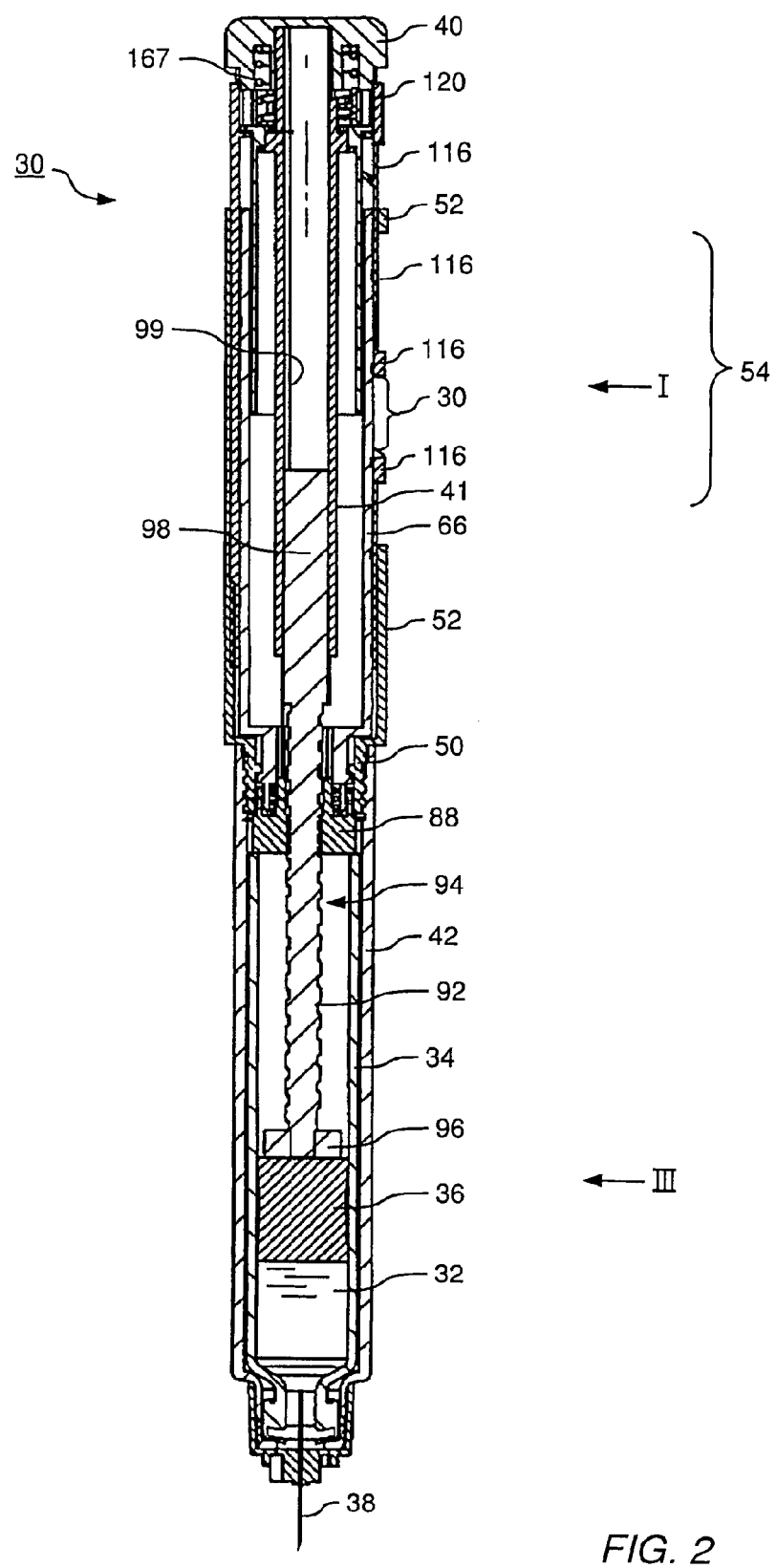
FIG. 2 is a section viewed along line II-II of FIG. 1.
Figure 6:
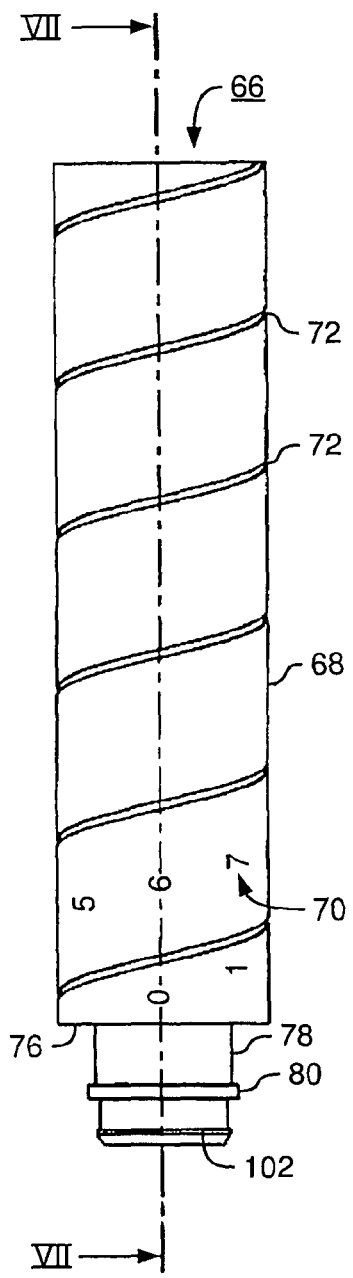
Figure 7:
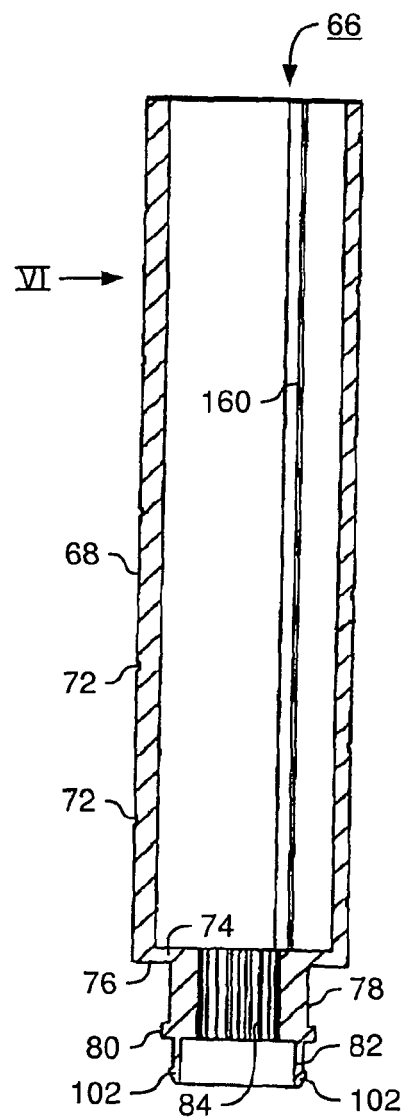
Figure 8:
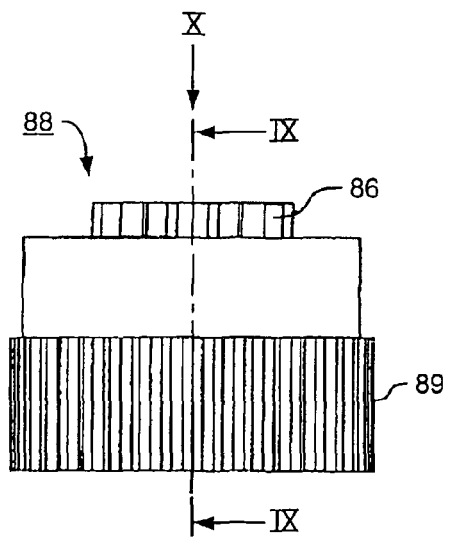
Figure 9:
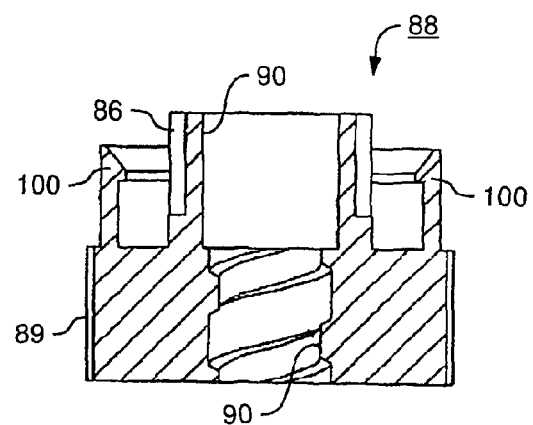
Figure 10:
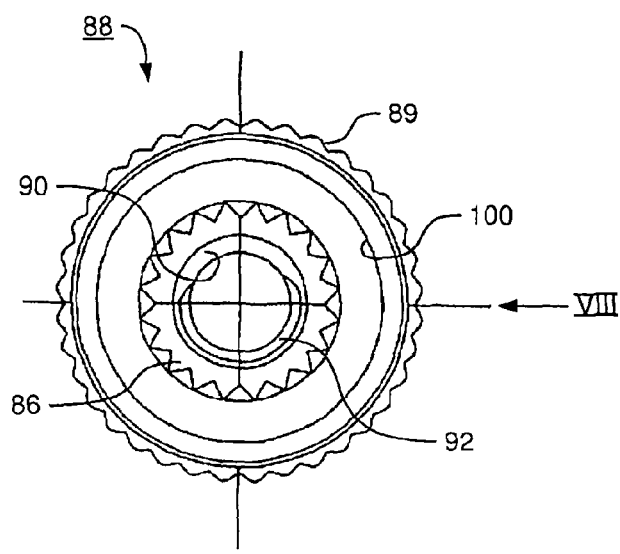
Figure 11:
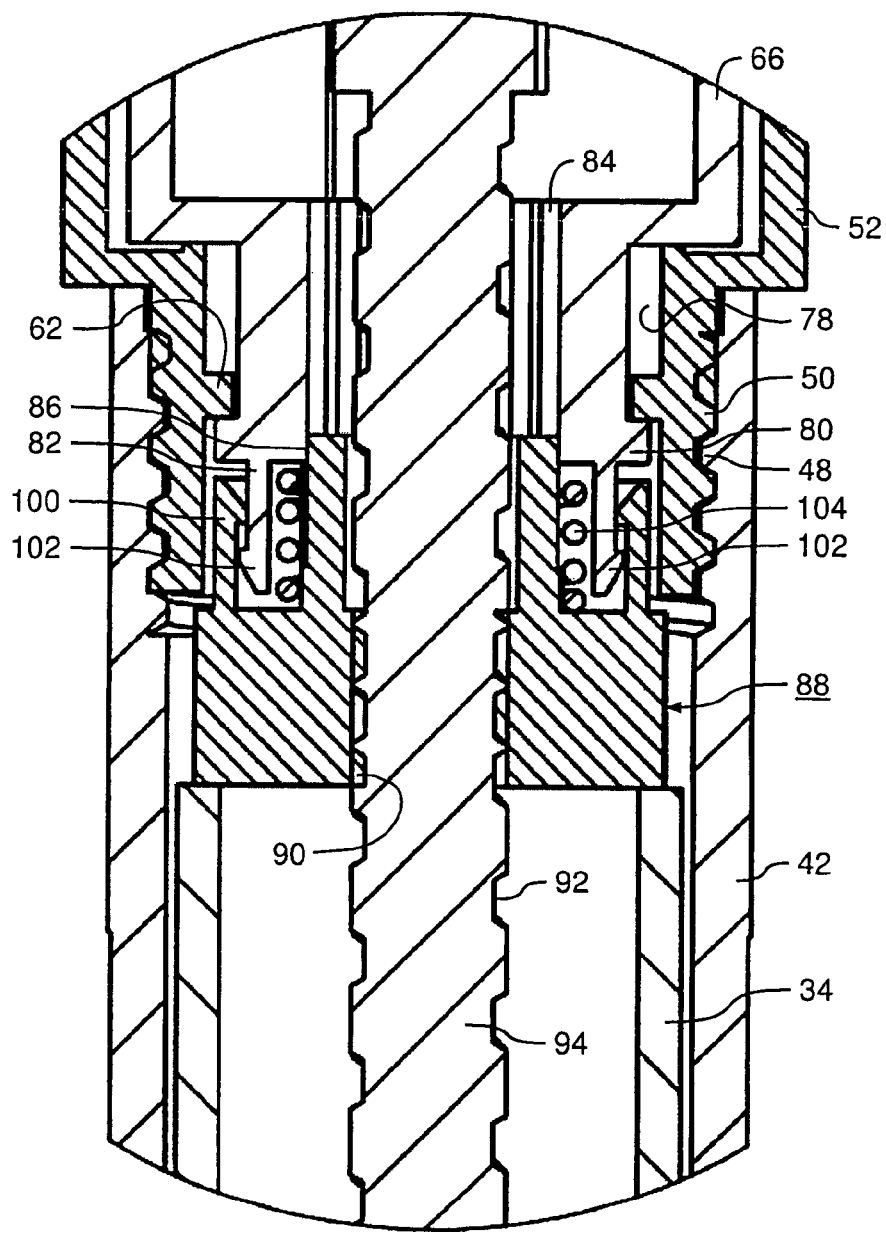
Figure 12:
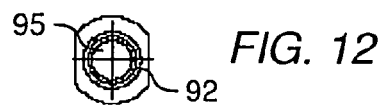
Figure 13:
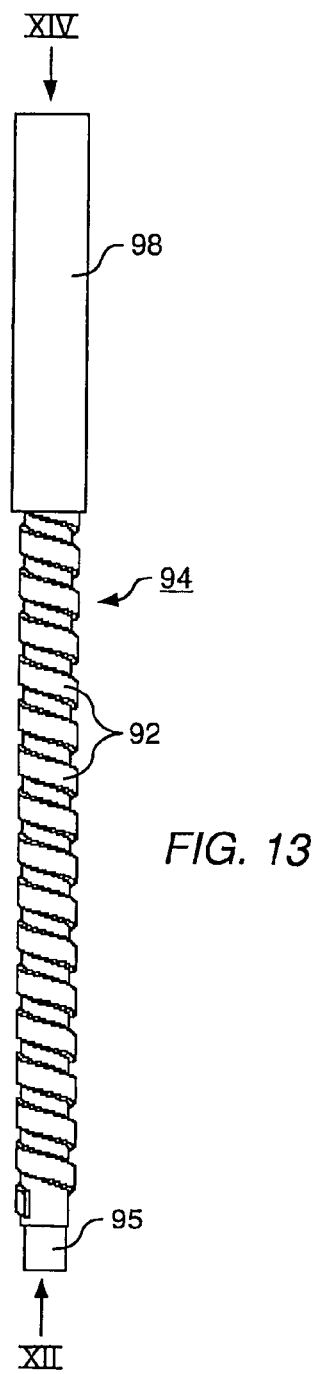
Figure 14:
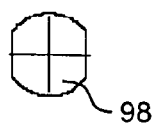
Figure 15:
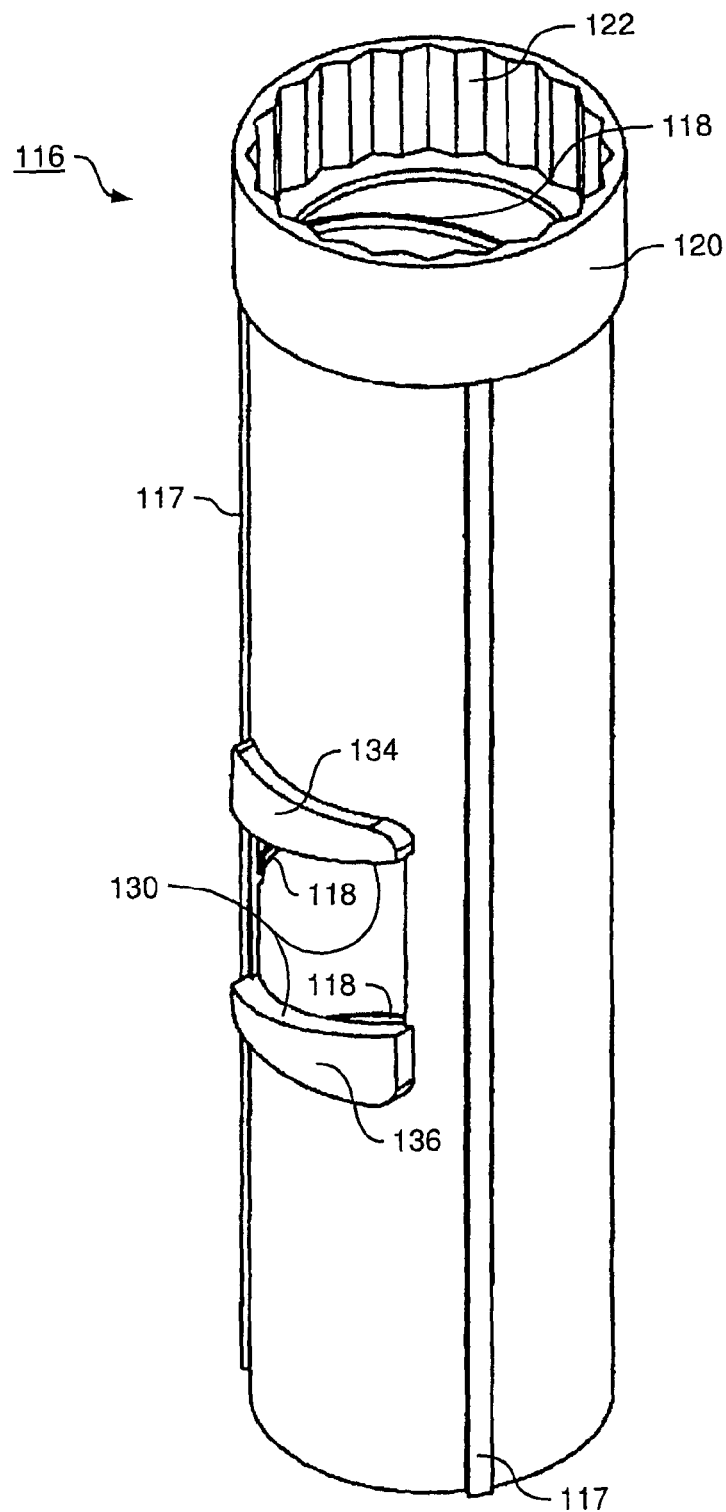
Figure 18:
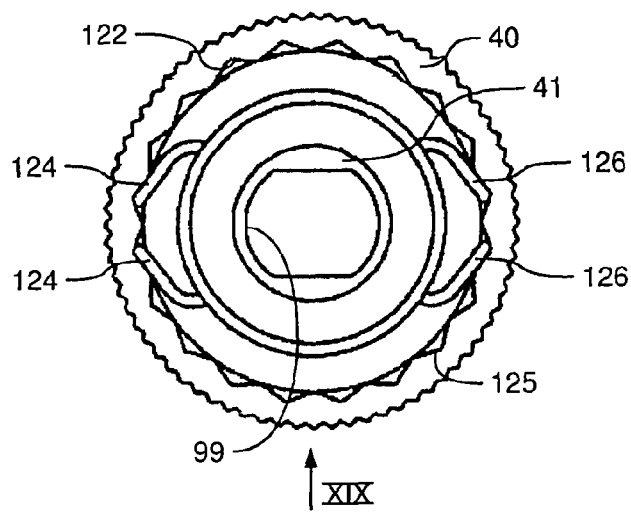
Figure 19:
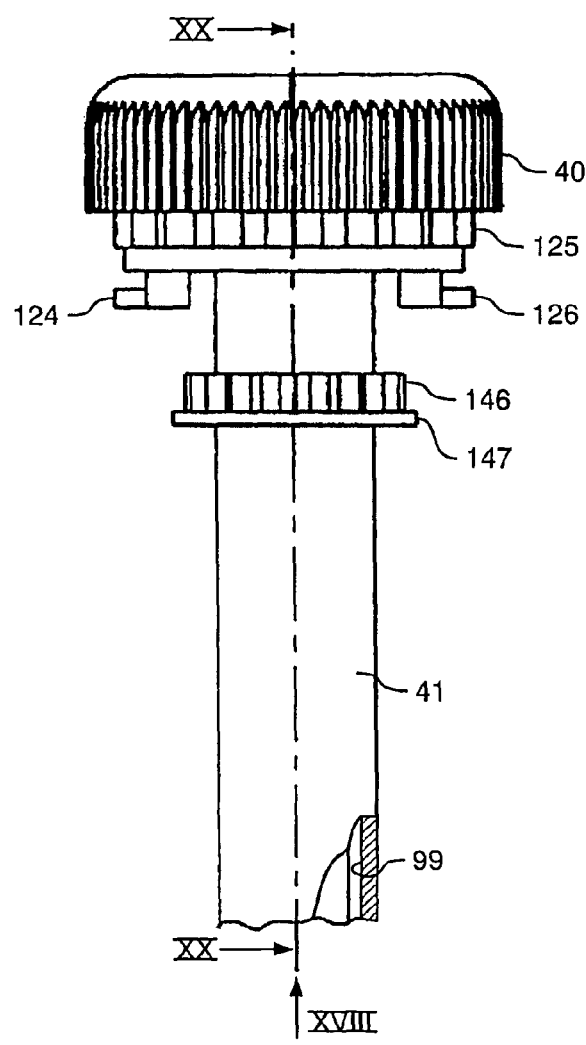
Figure 20:
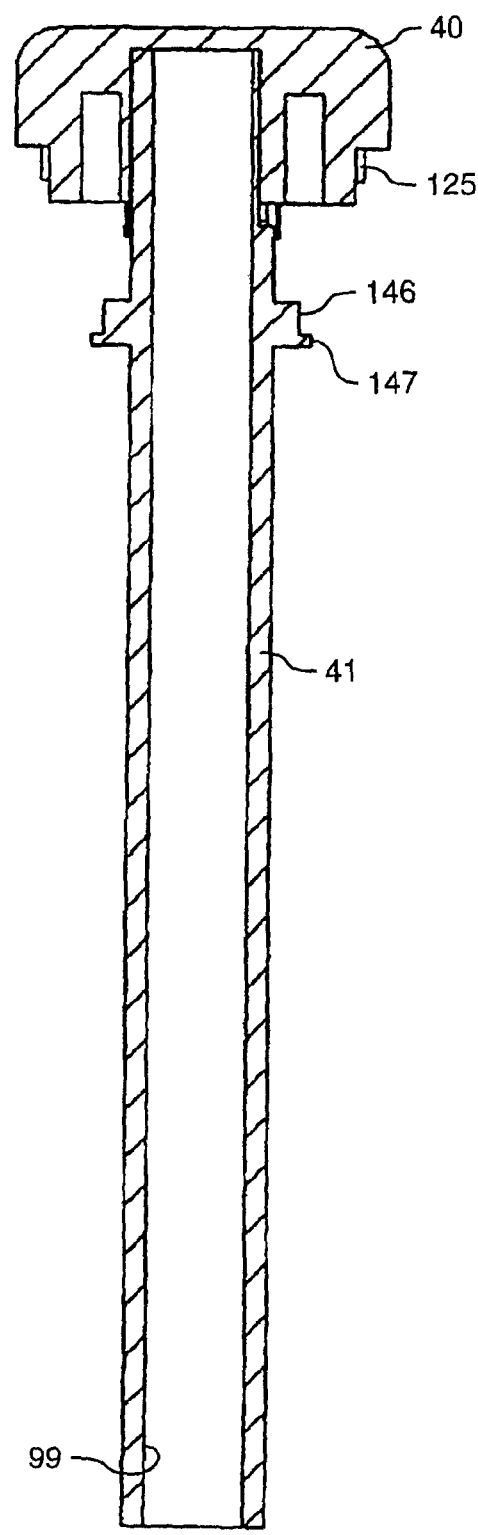
Figure 21:
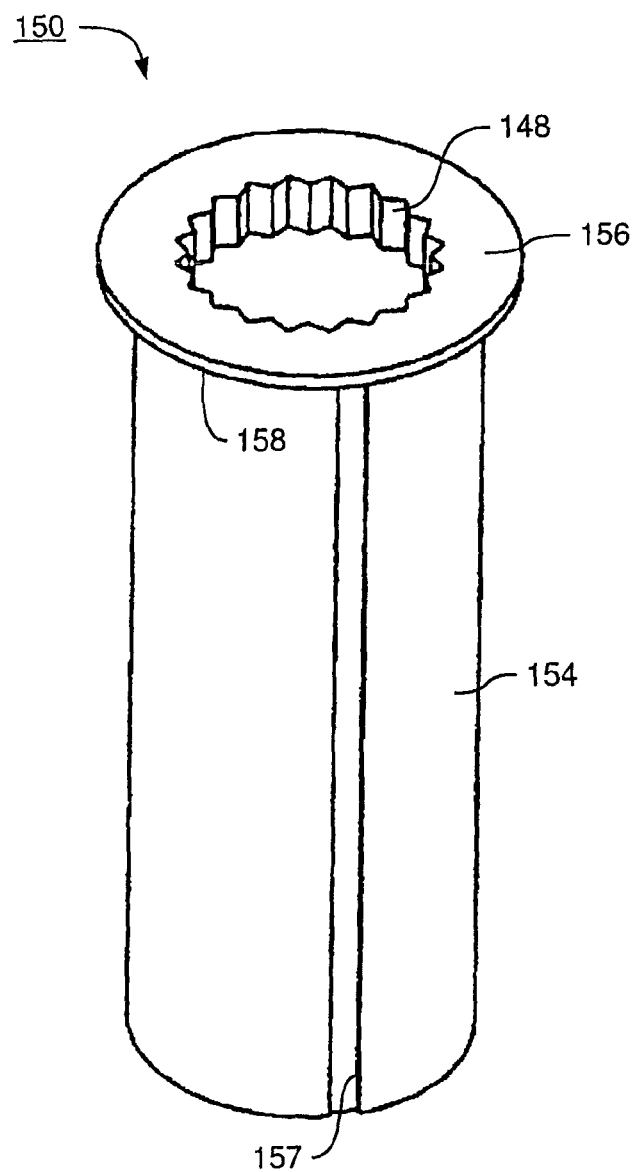
Figure 22:
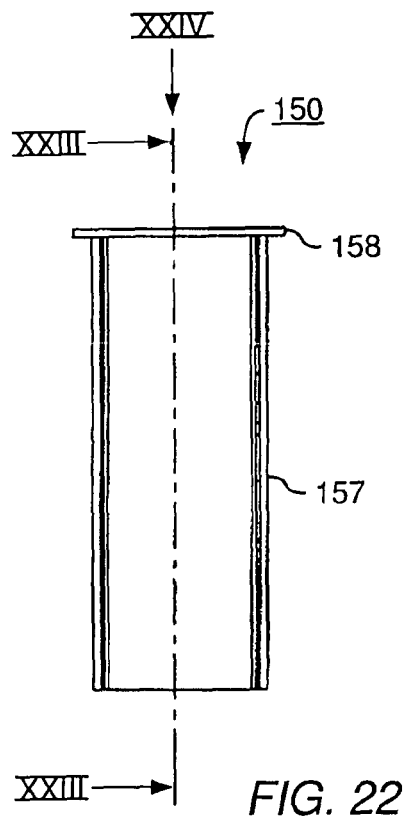
Figure 23:
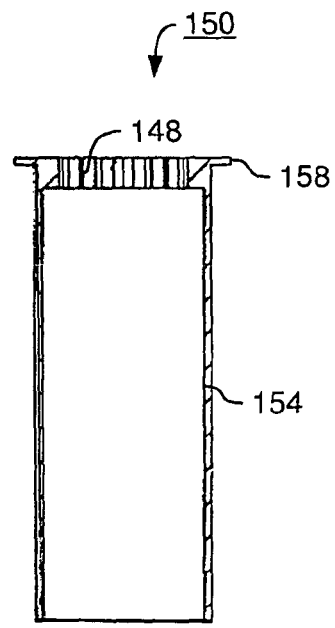
Figure 24:
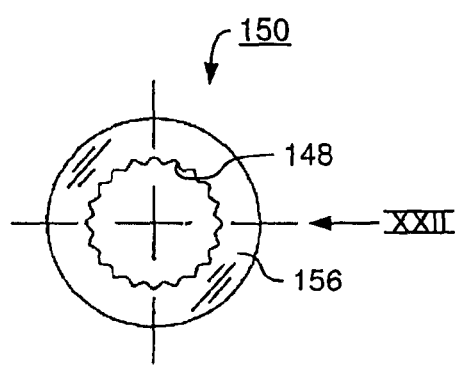
Figure 25:
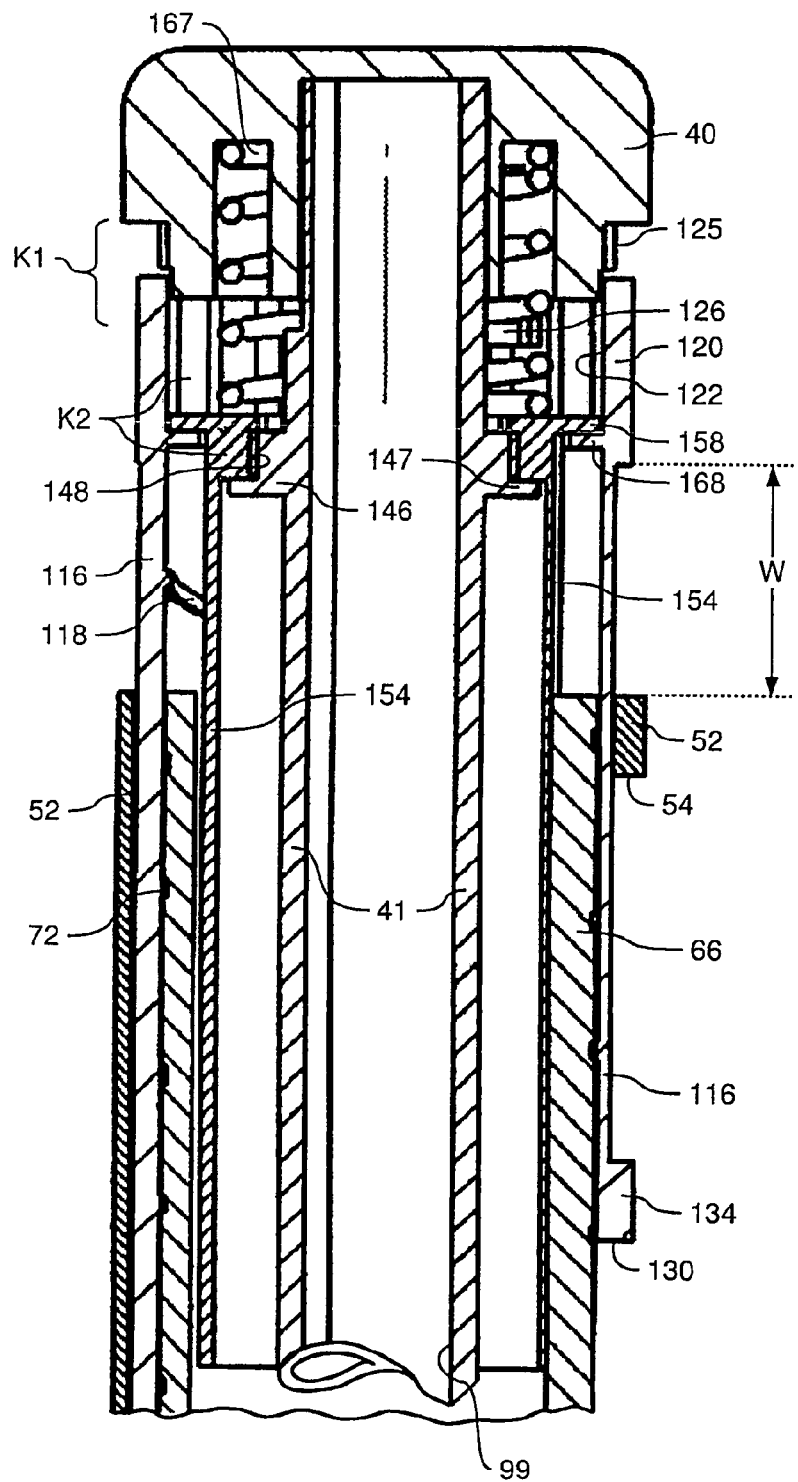
Figure 26:
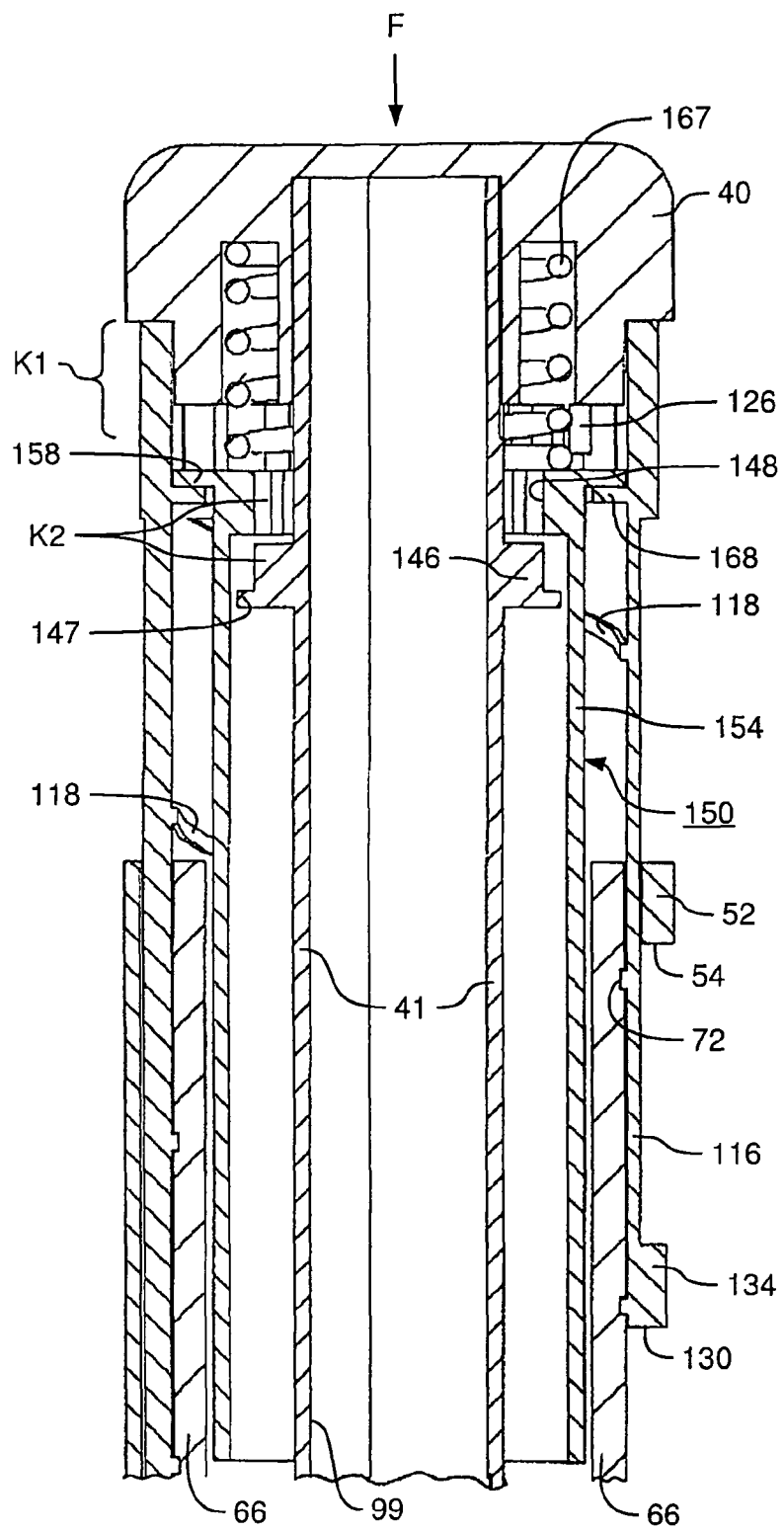
Figure 27:
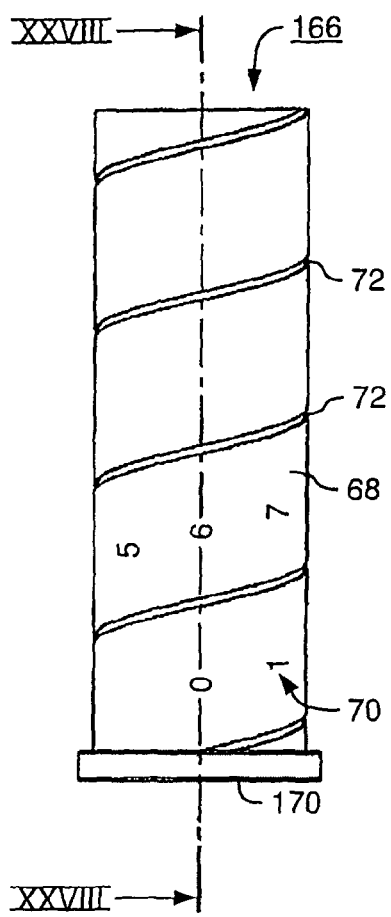
Figure 28:
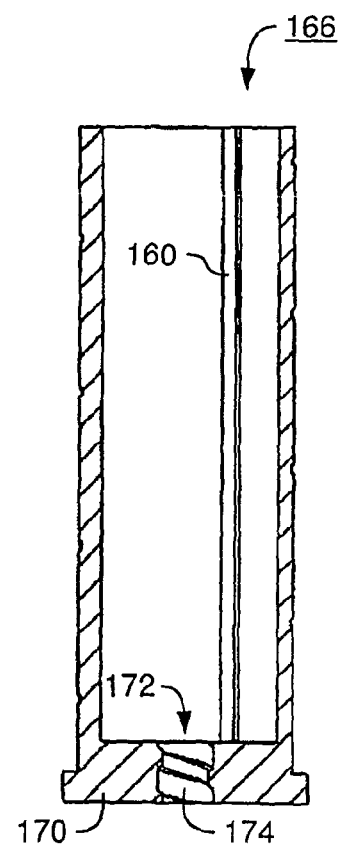
Figure 29:
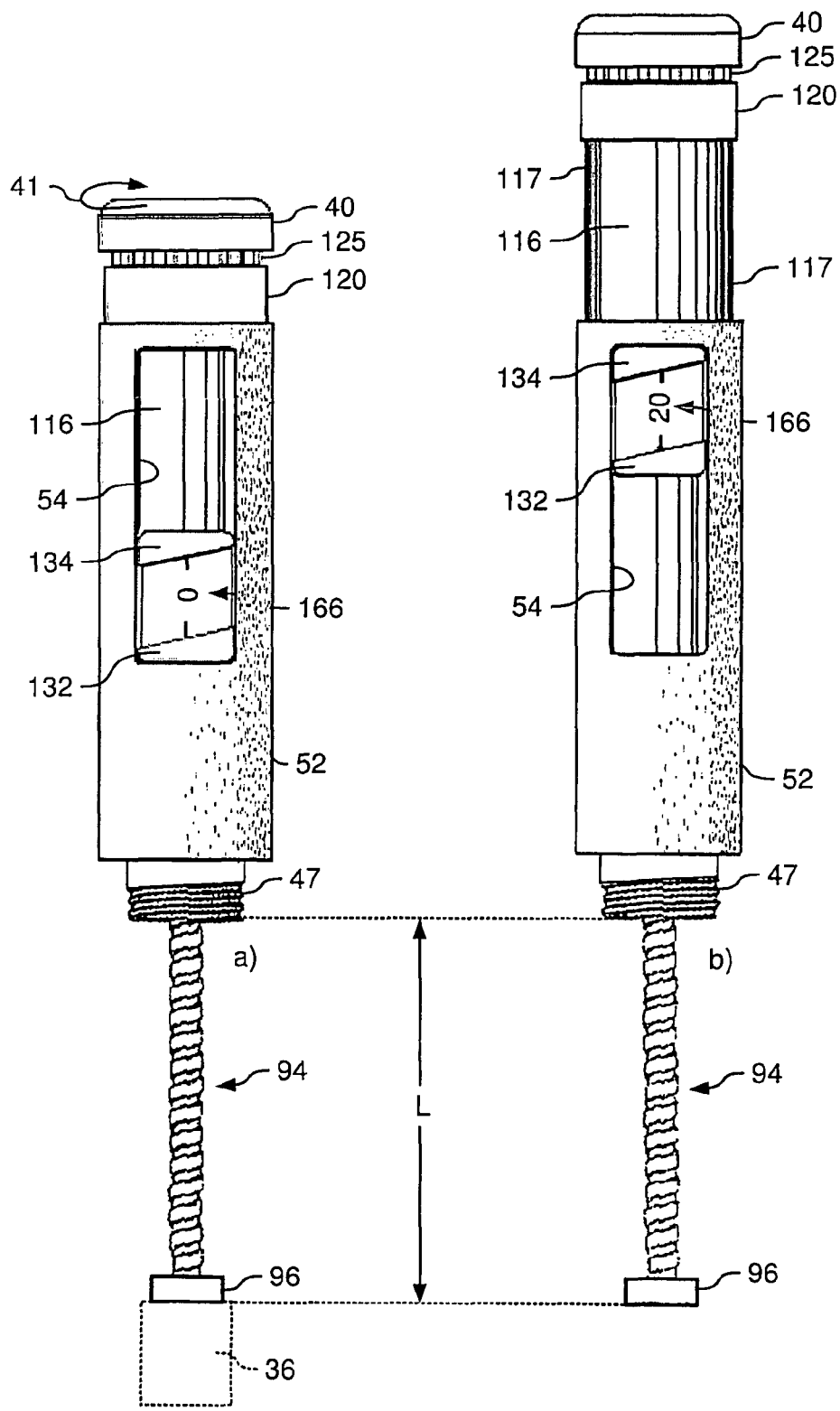
Figure 30:
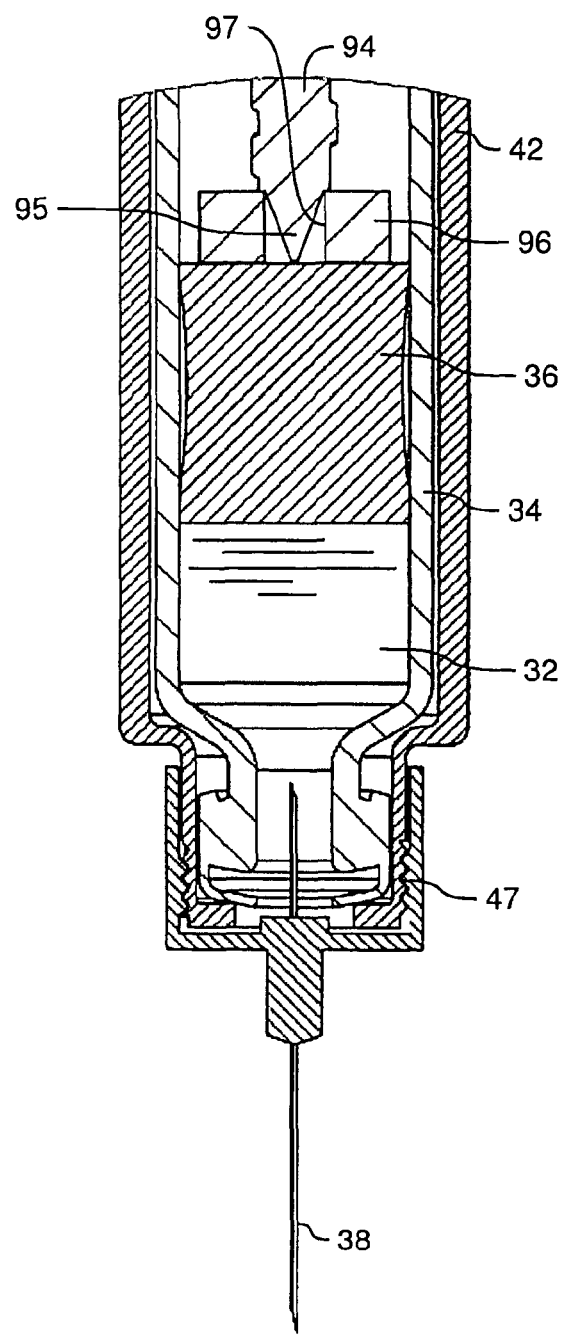
Figure 31:
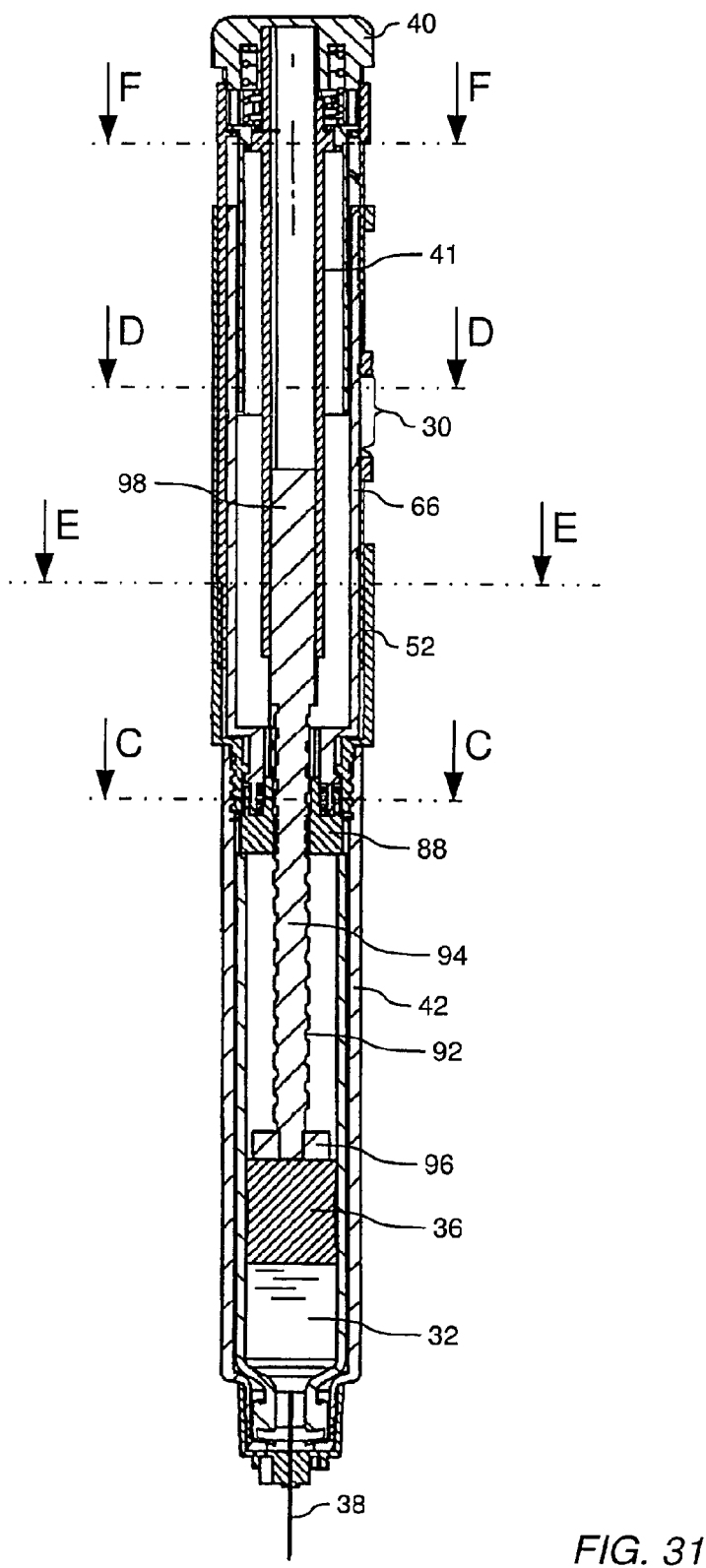
Figure 32:
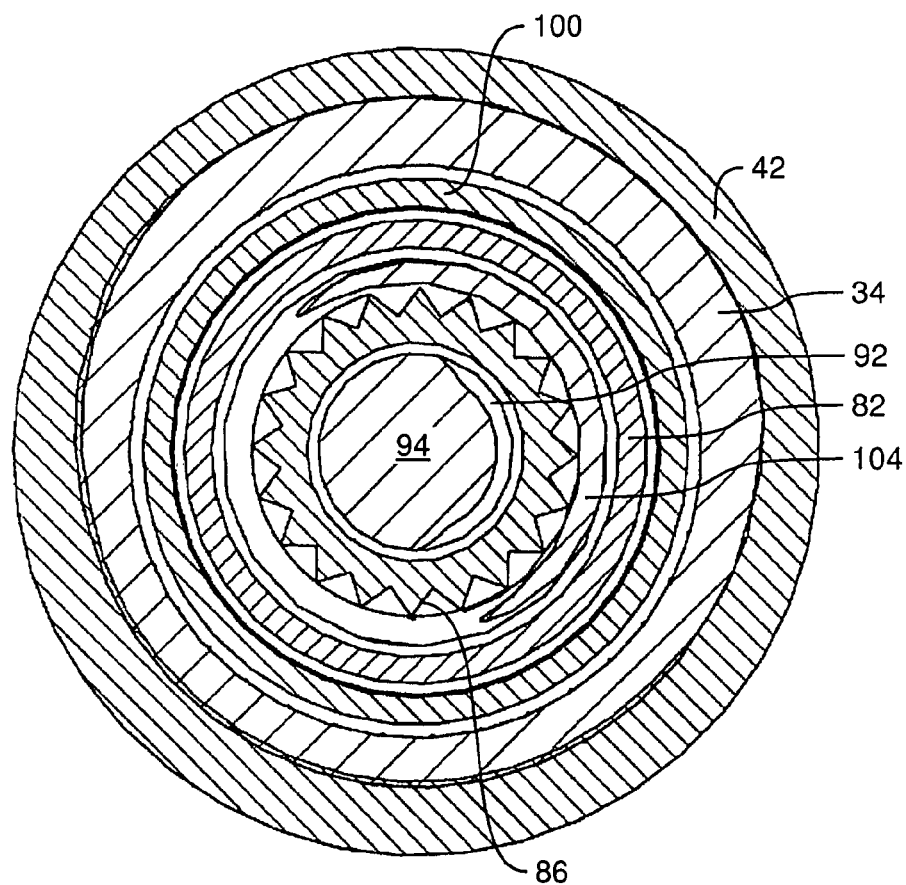
Figure 33:
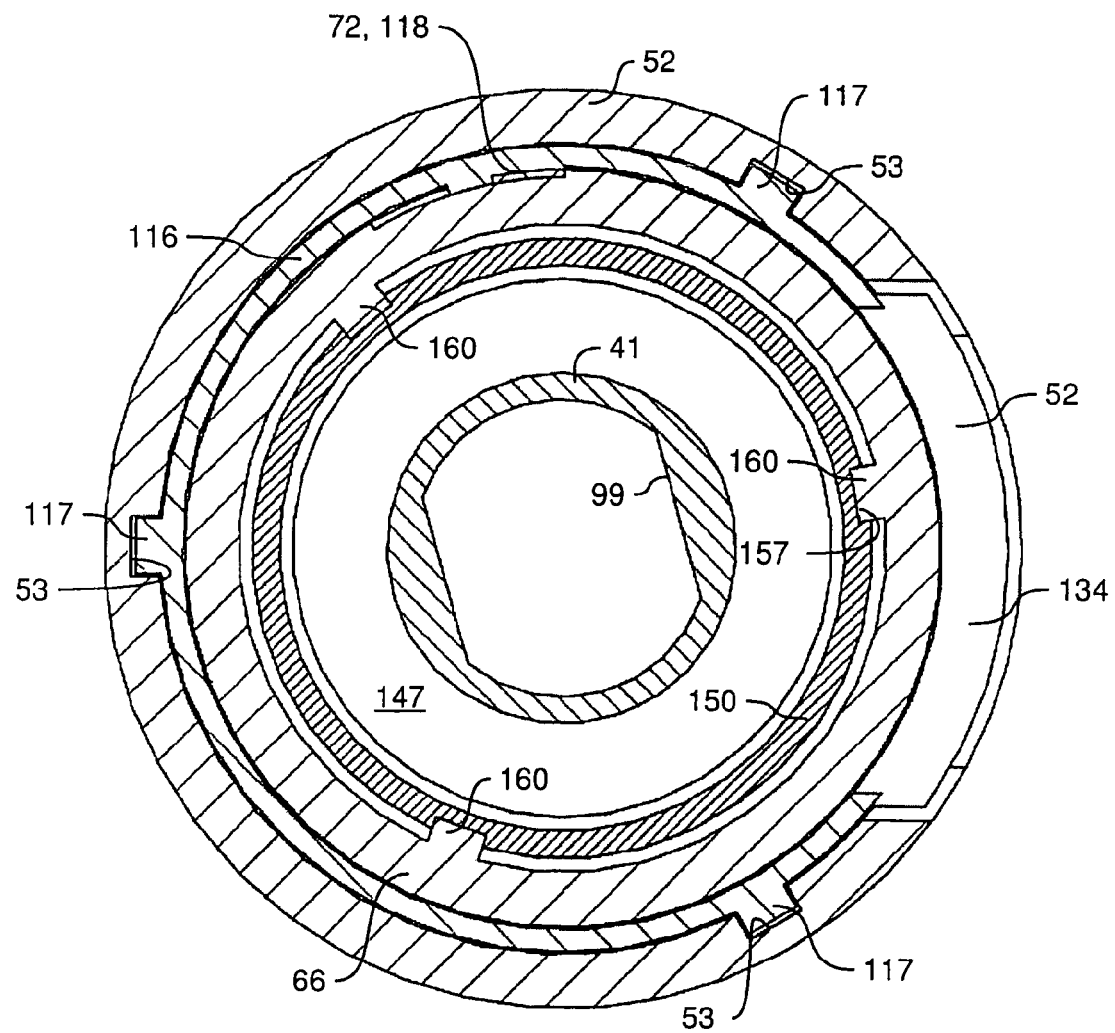
Figure 34:
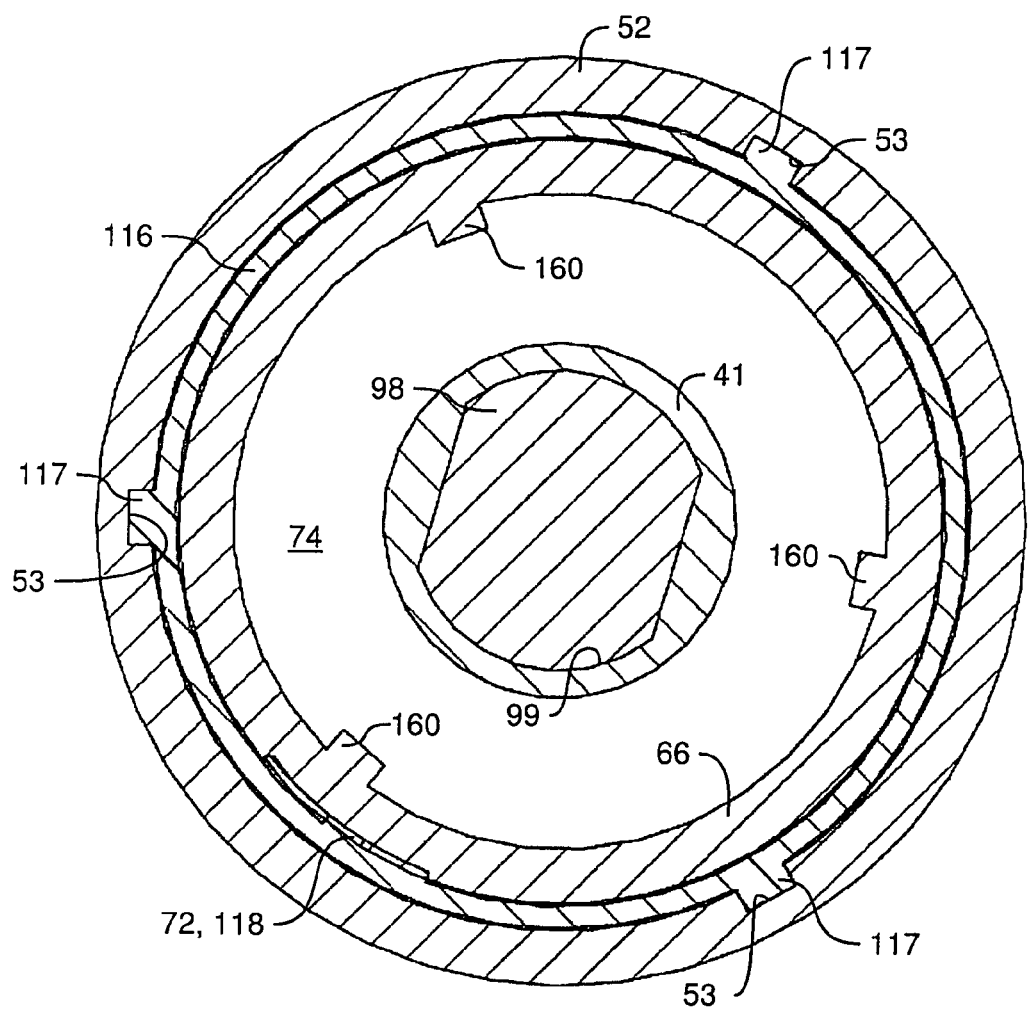
Figure 35:
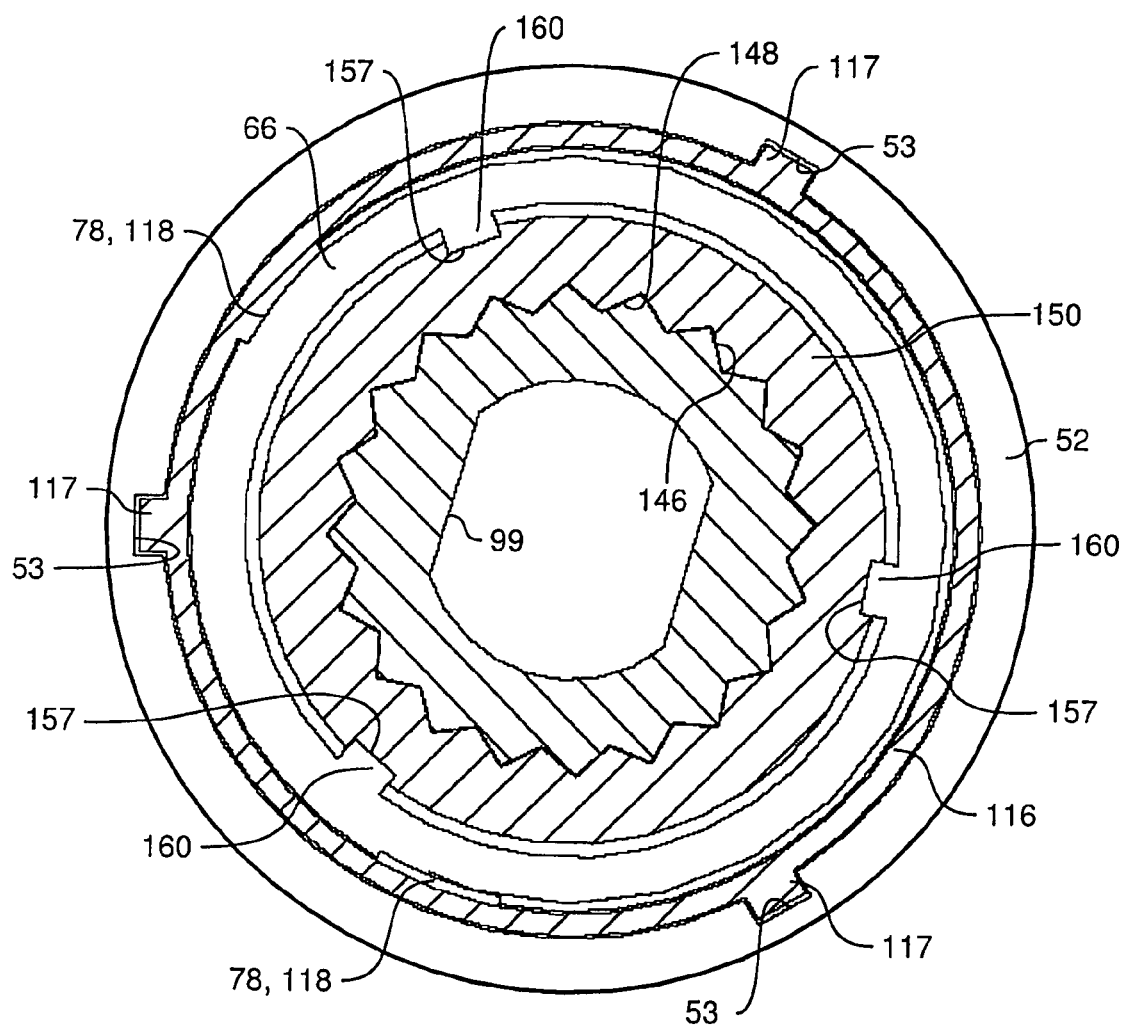

FIG. 5a) is a side view of a housing part 52 visible at the top of FIG. 1, viewed in the direction of arrow Va of FIG. 5b);

FIG. 5b) is a section viewed along line Vb-Vb of FIG. 5a);

FIG. 5c) is a side view viewed in the direction of arrow Vc of FIG. 5b);

FIG. 6 is a side view of a metering element (graduated tube) 66 serving to display a dose that has been set, viewed in the direction of arrow VI of FIG. 7;

FIG. 7 is a section viewed along line VII-VII of FIG. 6;

FIG. 8 is a side view of a nut 88 effective in the context of an injection, viewed in the direction of arrow VIII of FIG. 10;

FIG. 9 is a section viewed along line IX-IX of FIG. 8;

FIG. 10 is a plan view of the nut, viewed in the direction of arrow X of FIG. 8;

FIG. 11 is a section through nut 88 of FIGS. 8 to 10 in the assembled state;

FIG. 12 is a plan view of the lower end of a piston rod 94 depicted in FIG. 13, viewed in the direction of arrow XII of FIG. 13;

FIG. 13 is a side view of piston rod 94;

FIG. 14 is a plan view of the upper end of piston rod 94, viewed in the direction of arrow XIV of FIG. 13;

FIG. 15 depicts an injection sleeve 116 that is equipped with a window 130 that is effective in the context of dose display;

FIG. 16 is a side view of injection sleeve 116;

FIG. 17 is a section viewed along line XVII-XVII of FIG. 16;

FIG. 18 is view of a rotary and injection knob 40 that serves for the operation of injection device 30, viewed in the direction of arrow XVIII of FIG. 19;

FIG. 19 is a partly sectioned side view of the rotary knob, viewed in the direction of arrow XIX of FIG. 18;

FIG. 20 is a longitudinal section viewed along line XX-XX of FIG. 19;

FIG. 21 is a perspective depiction of a driver 150 that serves, in the context of dose setting, to transfer a rotary motion of rotary knob 40 to metering element (graduated tube) 66;

FIG. 22 is a side view of driver 150, viewed in the direction of arrow XXII of FIG. 24;

FIG. 23 is a longitudinal section viewed in the direction of line XXIII-XXIII of FIG. 22;

FIG. 24 is a plan view from above of driver 150, viewed in the direction of arrow XXIV of FIG. 22;

FIG. 25 is a longitudinal section through the upper part of the injection device, analogous to FIG. 2 but with a zero injection dose and before dose setting begins;

FIG. 26 is a longitudinal section analogous to FIG. 25 but after completion of an injection;

FIG. 27 is a plan view of a metering element (graduated tube) 166 that is provided for a disposable injection device in which carpule 34 cannot be replaced once its contents are consumed;

FIG. 28 is a longitudinal section viewed along line XXVIII-XXVIII of FIG. 27;

FIG. 29 is a diagram to explain the manner of operation;

FIG. 30 depicts a particular aspect of piston rod 94;

FIG. 31 is a longitudinal section analogous to FIG. 2, in which various section planes have been plotted;

FIG. 32 is a section along line C-C of FIG. 31;

FIG. 33 is a section along line D-D of FIG. 31;

FIG. 34 is a section along line E-E of FIG. 31;

FIG. 35 is a section along line F-F of FIG. 31; and

Figure 36:
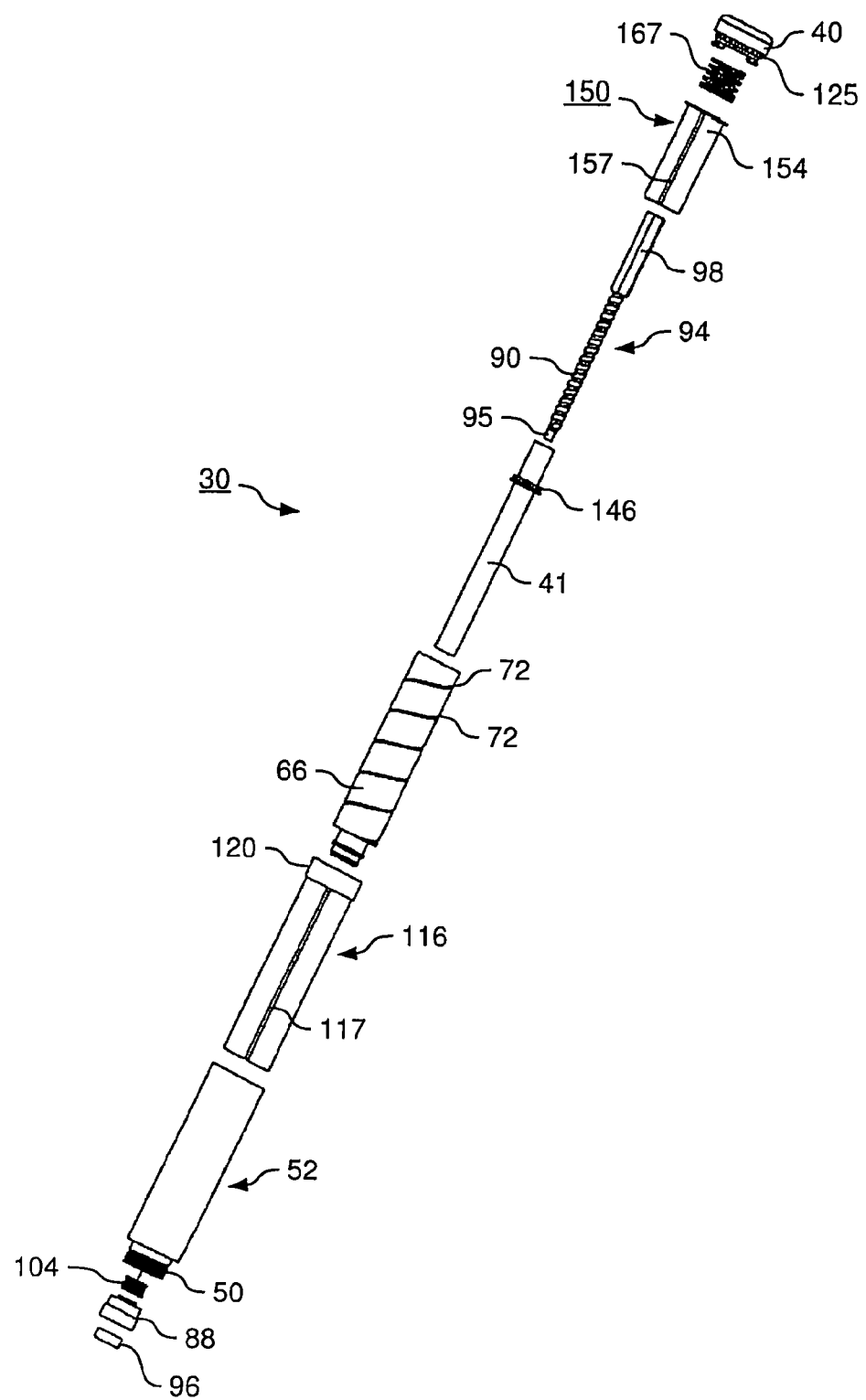

FIG. 36 is an exploded depiction to facilitate comprehension.

DETAILED DESCRIPTION

FIG. 1 shows, at greatly enlarged scale, a pen injector 30, viewed in the direction of arrow I of FIG. 2. It uses a reservoir, usually referred to as a carpule 34, for injection fluid 32. Located in this carpule 34 is a rubber piston 36, and when the latter is displaced from top to bottom (in FIG. 2), it presses injection fluid 32 out through an injection needle 38. Carpule 34 is a commercially usual part and is therefore not described further.

In the terminology usual in medicine, the terms "proximal" and "distal" are hereinafter used as follows:

proximal=toward the patient; in other words, in the direction of that end of injection device 30 at which needle 38 is located;

distal=away from the patient, i.e. in the direction of the upper (in FIGS. 1 and 2) end of device 30 at which a rotary knob 40 for setting the injection dose is located.

Be it noted that the terms "proximal" and "distal" are occasionally also used by medical non-professionals in the opposite sense, in which case these terms then refer to the doctor's hand.

Figure 3:
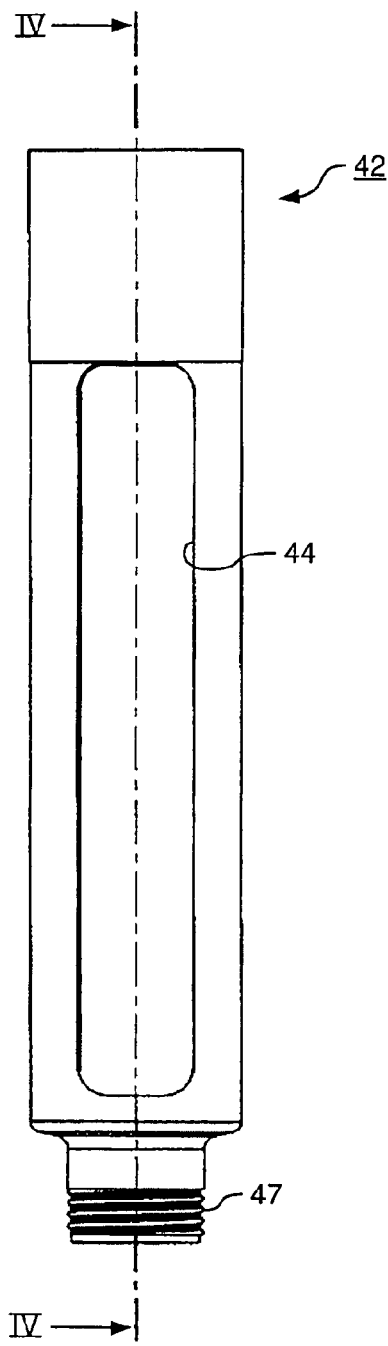
FIG. 3 is a side view of a housing part 42 that serves to receive a carpule 34 (see FIG. 2) having the fluid to be injected, viewed in the direction of arrow III of FIG. 2.
Figure 4:
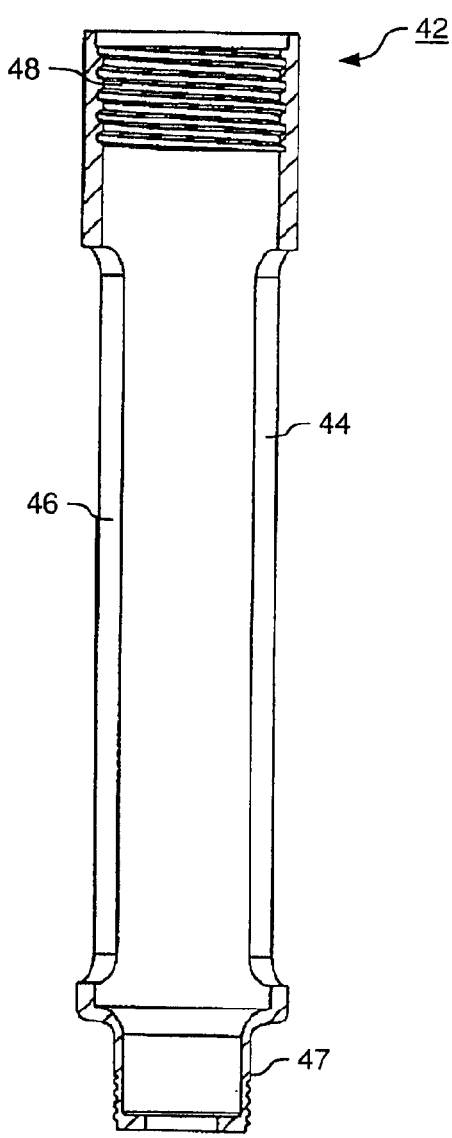
FIG. 4 is a section viewed along line IV-IV of FIG. 3.

A receiving part 42, which is depicted in FIGS. 3 and 4 and is also referred to as a carpule container, serves to receive carpule 34. Said part has two longitudinal windows 44, 46 through which the fill level in carpule 34 or the axial position of piston 36 can be observed, so that the patient can estimate, with the aid of graduations printed onto receiving part 42, the number of injection units that are still possible. Windows 44, 46 are not depicted in FIGS. 1 and 2.

Figure 5:
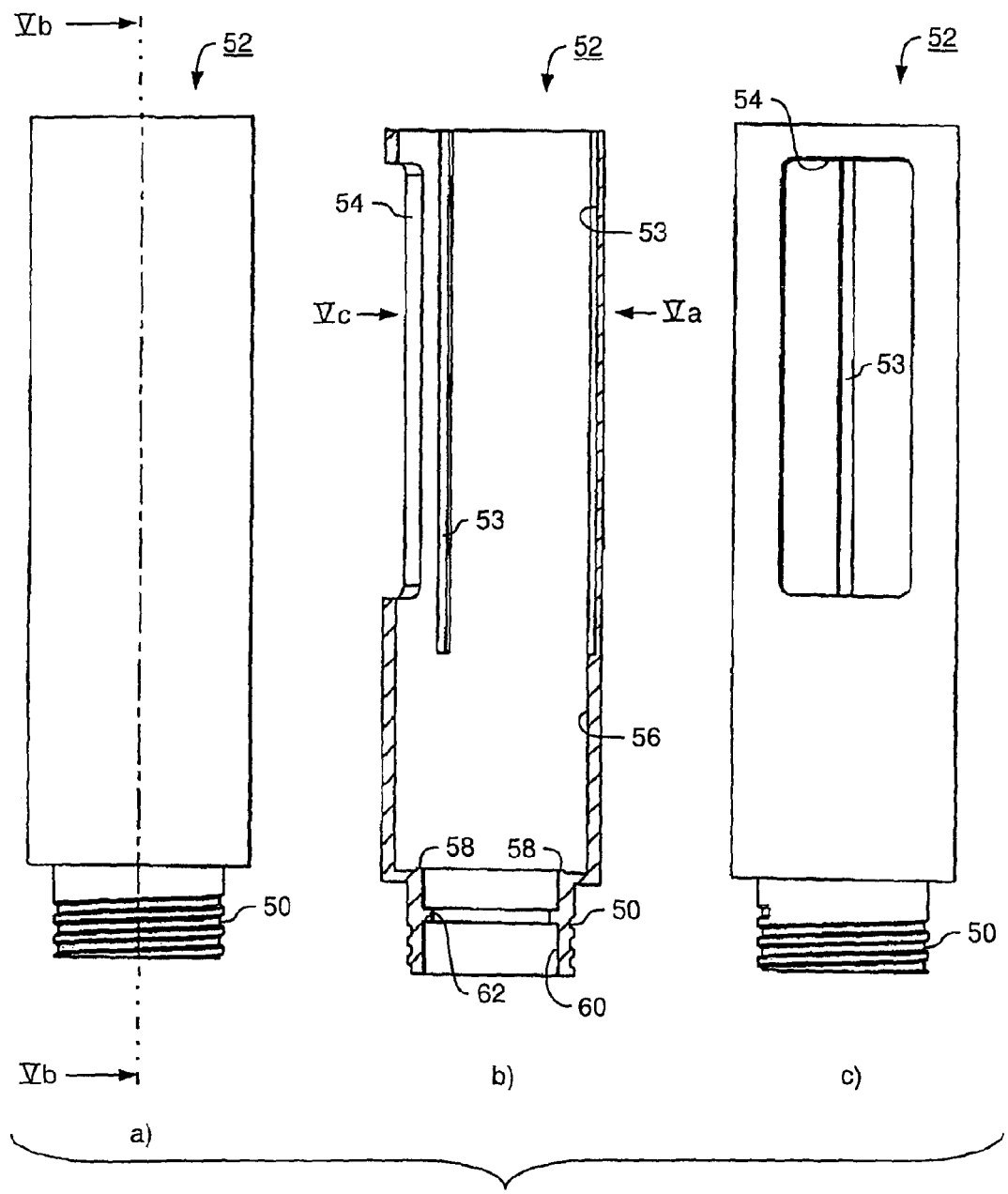

Receiving part 42 has, at the bottom, an external thread 47 for screwing on injection needle 48, and at the top an internal thread 48 that serves for connection to external thread 50 of an upper (in FIGS. 1 and 2) distal housing part 52 that is depicted in FIG. 5. Said part has a window 54 that serves for reading off the injection dose that has been set, and it has a cylindrical internal opening 56 that transitions at the bottom (in FIG. 5b)), via a shoulder 58 that serves as an axial bearing in the context of an injection, into an opening 60 of smaller diameter in which is located a shoulder 62 that serves for axial latching of metering element (graduated tube) 66 (FIGS. 6 and 7) in housing part 52. A corresponding rolling bearing could, for example, also be used instead of shoulder 58 as an axial bearing. Metering element 66 has a plurality of functions, and could therefore also be referred to as metering sleeve 66.

Metering element (graduated tube; metering sleeve) 66 is equipped on its cylindrical outer side 68 with numbers 70 to display the injection dose that has been set, and can therefore also be referred to as a graduated tube. Also located on this outer side 68 is an external thread 72 whose function will be explained below. Metering element (graduated tube) 66 transitions at its proximal end, via a shoulder 74 whose lower side 76 serves as a countermember for axial bearing 58 of FIG. 5b), into a cylindrical portion 78 of smaller diameter into which, in the assembled state, radial projection 62 (FIG. 5b) of housing 52 (FIG. 5b) engages, as shown e.g. by FIGS. 2 and 11. Portion 78 is delimited at the bottom by a radially projecting collar 80 that is adjoined at the bottom by a portion 82 having a slightly smaller outside diameter.

The inner side of portion 78 is equipped with an axial internal spline set 84 that serves for coupling to a complementary axial external spline set 86 that is located on a nut 88 that is depicted in FIGS. 8 to 11.

This nut 88 has an internal square thread 90 that is in engagement with external thread 92 of a piston rod 94 whose shape is best inferred from FIGS. 11 to 14. Said rod serves in the context of an injection, as shown in FIG. 2, to displace rubber piston 36 in a proximal direction, i.e. downward in FIG. 2, in order to inject injection fluid 32 through needle 38 into a patient. For this purpose, its external thread 92 is in engagement with an internal square thread 90 (depicted in FIGS. 9 and 10) of nut 88; and when, in the context of an injection, metering element (graduated tube) 66, and nut 88 nonrotatably coupled to it via axial spline sets 84, 86, is rotated clockwise as viewed from above, said element displaces piston rod 94, whose rotation is blocked during an injection, downward. In that context, piston rod 94 presses, with its proximal end and with an abutment plate 96 arranged thereon (FIG. 2), against rubber piston 36 and displaces it in the direction toward needle 38, so that fluid 32 is expelled there.

In order to prevent rotation during injection, piston rod 94 has at its distal part 98, which is depicted at the top in FIG. 13, a cross section (FIG. 12) that deviates from a circular shape, and this part is in positive engagement with an opening 99 (FIG. 18), complementary thereto, of rotary knob 40 (FIG. 2), so that blocking the rotation of rotary knob 40 also causes blocking of the rotation of piston rod 94, but an axial displacement is possible between rotary knob 40 and piston rod 94. This is described in detail below.

As FIGS. 9 and 11 show, nut 88 has upwardly projecting barbs 100 that are in engagement with corresponding barbs 102 at the lower end of metering element 66.

As FIG. 11 shows, a compression spring 104 is located between portion 82 and the portion having axial external spline set 86. This spring is compressed when, after insertion of a fresh carpule 34, internal thread 48 (FIG. 4) is screwed onto external thread 50 (FIG. 5), with the result that axial external spline set 86 (FIG. 8) of nut 88 becomes coupled nonrotatably to axial internal spline set 84 of metering element (graduated tube) 66 (see FIG. 11).

When a carpule 34 is replaced, spring 104 (FIG. 11) pushes axial spline sets 84, 86 apart from one another so that nut 88 can rotate freely. This allows the doctor or patient to rotate nut 88 by hand so that piston rod 94 is displaced in a distal direction until it comes to rest against nut 88, and space is created for the insertion of a fresh carpule 34.

Nut 88 is not required for a disposable injector, and FIGS. 27 and 28 show a simplified solution for this instance, in which a thread 174 that interacts with the external thread (92) of piston rod 94 is likewise provided in a metering element (graduated tube) 166.

A sleeve-shaped element in the form of an injection sleeve 116, which is depicted in FIGS. 15 to 17, is provided for engagement into external thread 72 of metering element (graduated tube) 66. As FIG. 2 shows, said sleeve is arranged between metering element (graduated tube) 66 and housing 52, and has an internal thread 118 (FIG. 17) that is in engagement with external thread 72 of metering element (graduated tube) 66 (FIG. 6) or 166 (FIG. 28), so that when injection sleeve 116 is rotated counterclockwise (as viewed from above) with the aid of rotary knob 40 in the context of dose setting, injection sleeve 116 is displaced upward on external thread 72 of metering element (graduated tube) 66, as depicted in FIGS. 1 and 2 for a small injection dose. The same is true analogously for graduated tube 166 of FIGS. 27 and 28.

Injection sleeve 116 has, at the top, an extension 120 having an axial internal spline set 122 that has a variety of functions:

a) As shown in FIGS. 19, 20, 25, and 26, tube 41 is fixedly connected to rotary knob 40, and an external spline set 146 is provided on tube 41. Like external spline set 125 of rotary knob 40, this set is part of two couplings K1 and K2 (see FIGS. 25 and 26), and these couplings can be actuated by displacing tube 41 by means of knob 40, or by means of a compression spring 167 in the latter, axially relative to injection sleeve 116. A comparison of FIGS. 25 and 26 shows this axial displacement.

It serves, in the context of an injection, to couple rotary knob 40 via coupling K1 to injection sleeve 116 in such a way that rotation between these two parts is blocked; in other words, when the patient (after having set a dose) presses with a force F in a proximal direction onto rotary knob 40, as shown in FIG. 26, injection sleeve 116 is moved in a proximal direction, in which context an axial external spline set 125

(FIG. 25) provided on rotary knob 40 engages into internal spline set 122. A rotation between injection sleeve 116 and rotary knob 40 is thereby blocked, and injection sleeve 116 is moved in a proximal direction; because of its longitudinal guidance (by grooves 53 of FIG. 5 and projections 117 of FIG. 15), it cannot rotate in housing 52. This axial motion of injection sleeve 116 is transformed by threads 72, 118 into a rotary motion of metering element (graduated tube) 66 (FIGS. 6 and 7).

This rotary motion also rotates nut 88 and thereby displaces piston rod 94 (which in this situation is prevented from rotating) in a proximal direction, so that rubber piston 36 is displaced in a proximal direction and an injection of fluid 32 takes place.

b) Also engaging into axial internal spline set 122 (FIGS. 15, 17, and 25) are two resilient ratchet members 124, 126 (FIG. 18) that are arranged on the inner side of rotary knob 40. They become effective in the context of dose setting, since here external spline set 125 of rotary knob 40 is not in engagement with axial internal spline set 122 of injection sleeve 116 (FIG. 15), and rotary knob 40 can thus rotate relative to said axial internal spline set 122, making it possible even for patients with poor vision to set a dose by counting the clicks generated in the context of the rotary motion.

The axial motion of injection sleeve 116 in the context of dose setting and injection also results in an axial displacement of window 130 (FIGS. 15 to 17), which is provided in casing portion 132 of injection sleeve 116 and is delimited at the top by a thickened casing part 134 and at the bottom by a thickened casing part 136. These thickened casing parts 134, 136 are guided in window 54 (FIGS. 1, 2, and 5) of upper housing part 52. They move upward in window 54 in the context of dose setting and move downward in window 54 during an injection, dose 70 that is to be injected being continuously displayed in window 130 as a result of the simultaneous rotation of metering element (graduated tube) 66. This dose display consequently decreases during an injection, and thereby indicates to the patient how much he or she still has to inject. The patient can thus constantly monitor injection progress during the injection operation, and thus knows exactly when the injection is complete as the "0" display appears in the viewing window, and he or she can therefore pull the injection needle out of his or her fatty tissue without losing injection fluid.

As FIGS. 19 and 20 show, an external spline set 146 is provided on tube 41 that is connected to rotary knob 40; this set, like external spline set 125, is a part of couplings K1 and K2 (FIGS. 25, 26) that is actuated by an axial displacement of tube 41 (by means of knob 40 or compression spring 167 associated therewith).

External spline set 146 is closed off at the bottom by a plate-like flange 147, and interacts with an internal spline set 148, complementary to the first set, of a driver 150 that is depicted in FIGS. 21 to 24. As FIGS. 21 to 24 clearly show, driver 150 has approximately the shape of a cylindrical tube 154 that is closed off at the top by a kind of flange 156 that protrudes, with a rim 158, radially beyond tube 154. Axial internal spline set 148 is located at the center of flange 156. Tube 154 is equipped with a guide groove 157 that interacts with a corresponding projection 160 (FIG. 7) on the inner side of metering element (graduated tube) 66 or 166 (FIG. 28) so that a rotation of driver 150 (in order to set a dose) produces a corresponding rotation of metering element (graduated tube) 66.

Located in rotary knob 40 is compression spring 167, which biases rotary knob 40, and tube 41 connected to it, in an upward direction (see FIG. 25) so that upper coupling K1 (FIGS. 25, 26) constituted by axial external spline set 125 (of rotary knob 40) and axial internal spline set 122 (of injection sleeve 116) is opened because axial external spline set 125 is not engaging into axial internal spline set 122 of injection sleeve 116. It thereby becomes possible to set a desired injection dose because, in this position, lower coupling K2 (FIG. 25) is closed because axial external spline set 146 (FIGS. 19, 20; on tube 41) is engaging into axial internal spline set 148 (FIG. 21) of driver 150, the engagement motion being limited by flange 147. Rim 158 of flange 156 is then braced against a shoulder 168 in the interior of injection sleeve 116 (see FIG. 26).

In this position, when knob 40 is then rotated it rotates driver 150, by tube 41 and axial external spline set 146 (FIG. 20) located on it as well as internal spline set 148 (FIG. 21), and said driver, by its groove 157, rotates graduated tube 166. Injection sleeve 116 is thereby displaced in a distal direction, i.e. axially upward, and window 130 along with it. Nut 88 is also rotated along with the rotation of graduated tube 66, but this has no influence on the location of rubber piston 36, since piston rod 94 also rotates together with nut 88 so that the former cannot change its axial location.

In the position as shown in FIG. 25, upper coupling K1 is therefore open and lower coupling K2 is closed, so that upon a rotation of knob 40 both piston rod 94 and nut 88 rotate in the same direction and at the same speed; and the position of piston rod 94 consequently cannot change because of course it is coupled nonrotatably, but axially displaceably, to tube 41.

Injection sleeve 116 together with rotary knob 40 does, on the other hand, become displaced upward, i.e. in a distal direction, as a result of such a rotary motion, and the dose that has been set is correctly displayed in window 130, as depicted in FIG. 29.

FIG. 26 shows the situation in the context of an injection. The patient firstly inserts needle 38 (FIGS. 1, 2, 30) and then presses with a force F (FIG. 26) on rotary knob 40. He or she thereby opens coupling K2 and closes coupling K1, thereby nonrotatably connecting tube 41, and piston rod 94 guided therein (see FIG. 2), to injection sleeve 116 and consequently to housing 52, so that piston rod 94 can now no longer rotate relative to housing 52.

As a result of (the patient's) force F, injection sleeve 116 is displaced downward, over the distance previously (FIG. 25) selected, into the zero position, and as a result of the threaded connection between internal thread 118 of injection sleeve 116 and external thread 72 of metering element (graduated tube) 66, rotates said graduated tube and, with it, nut 88 (FIGS. 8 to 10) so that piston rod 94, which cannot rotate, is moved by the rotation of nut 88, and of internal thread 90 provided therein, in a proximal direction and brings about an injection, by displacing rubber piston 36 in a proximal direction by an amount equal to the dose that was set.

A mechanical conversion ratio can be provided in this context, i.e. a displacement of injection sleeve 116 over a preset distance D causes piston rod 94 to move a distance D/f, where f can assume values between approximately 0.5 and 2, depending on the design of the thread pitches. This enables a more accurate dose display for small injection doses, and has proven to be advantageous especially for patients having poor vision.

FIGS. 27 and 28 show a graduated tube 166 for a so-called disposable injection device (depicted here only in part), i.e. for an injection device in which carpule 34 (not depicted in FIGS. 27 and 28) cannot be replaced. The injection device must therefore be discarded once the carpule is empty. The construction of metering element (graduated tube) 166 corresponds largely to that of metering element (graduated tube)

66 according to FIGS. 6 and 7, i.e. graduated tube 166 also has on its outer side 68 an external thread 72 and graduated values 70, and internally it has a projection 160 for longitudinal guidance in a longitudinal groove 157 of driver 150 (see FIGS. 21 to 24). Metering element (graduated tube) 166 of FIGS. 27 and 28 also has at its proximal end a base 170 in which a threaded orifice 172 having an internal square thread 174 is located. Piston rod 94 is screwed with its external thread 92 into this threaded orifice 172, similarly to what is shown in FIG. 11. Because, in this case, piston rod 94 cannot be returned to its position prior to the first injection once the contents of carpule 34 have been exhausted, the device must be disposed of after use.

Cartridge Replacement

In the version according to FIG. 11, the two housing parts 52, 42 are unscrewed from one another when carpule 34 needs to be replaced. The connection from metering element 66 to part 88 is thereby interrupted (by the action of compression spring 104) so that part 88 can be freely rotated by hand and the patient can thread piston rod 94 upward in a distal direction until it stops. Once the exhausted carpule 34 is taken out, a fresh carpule can then be inserted and, after the usual setting steps prior to the first injection, the patient can once again make injections normally.

FIG. 29 shows the dose setting procedure; carpule 34 and carpule container 42 are not depicted, so that the illustration is more informative. Rubber piston 36 of carpule 34 is indicated with dot-dash lines.

Looking in FIG. 29a) from above, i.e. in a proximal direction, onto rotary knob 40, the latter is rotated clockwise (arrow 41) in order to set a dose. Piston rod 94 thereby rotates, but so does nut 88 (FIG. 11), so that piston rod 94 projects the same length L out of housing 52 both at a dose of zero and at any dose that can be set. Injection sleeve 116, however, does become displaced upward out of housing 52 in the context of the setting process; FIG. 29b) shows the maximum dose that can be set, the value of which may differ depending on how the device is used. The value "20" that is depicted is therefore to be understood as merely an example.

Dose setting is accomplished here by an axial displacement of injection sleeve 116 in a distal direction, whereas the location of plate 96 relative to rubber piston 36 does not change as the dose is set.

Because piston rod 94 rotates relative to rubber piston 36 as the dose is set, it is advisable to use, at proximal end 95 (FIG. 30) of piston rod 94, a plate 96 having an opening 97 in which proximal end 95 of piston rod 94 can rotate with little friction. As FIG. 30 shows, proximal end 95 of piston rod tapers downward so that the friction there between end 95 and rubber piston 36 becomes low.

The actual injection, by means of axial pressure on rotary knob 40 with force F, has already been described with reference to FIG. 26, to which the reader is therefore referred.

FIG. 31 shows a longitudinal section analogous to FIG. 2 in which four different horizontal sections C-C, D-D, E-E, and F-F are plotted. The reference characters are the same as in the preceding Figures, and this is not a disposable syringe.

FIG. 32 shows carpule container 42 on the outside, barbs 100 therein, then barbs 82 and spring 104, as well as external spline set 86 of part 88 and, all the way on the inside, piston rod 94 with its external thread 92.

FIG. 33 shows that tube 41 has an axial opening 99 in which part 98 (FIGS. 12 and 13) of piston rod 94 is guided nonrotatably but longitudinally displaceably. This makes it possible, by pushing rotary knob 40 (see FIG. 26), to connect piston rod 94 to housing 52 in such a way that tube 41 cannot rotate relative to housing 52.

Three longitudinal ribs 117, which are guided in corresponding longitudinal grooves 53 (FIG. 5) of housing 52, are provided on injection sleeve 116.

A screw connection 72, 118 is provided between injection sleeve 116 and metering element (graduated tube) 66. Metering element (graduated tube) 66 has three longitudinal ribs 160 that are guided in corresponding longitudinal grooves 157 of driver 150.

FIG. 34 shows, on the outside, housing 52 with its three longitudinal grooves 53 in which injection sleeve 116 is guided with its three longitudinal ribs 117. On its inner side, injection sleeve 116 is connected via threads 72, 118 to metering element (graduated tube) 66, which in turn is equipped on its inner side with three longitudinal ribs 160.

FIG. 35 shows section F-F of FIG. 31. On the outside is housing 52 in which (as shown in FIG. 5) are provided longitudinal grooves 53 into which three corresponding ribs 117 of injection sleeve 116 engage. The inner side of injection sleeve 116 is connected via threads 72, 118 to the outer side of metering element (graduated tube) 66. The inner side of metering element (graduated tube) 66 has three longitudinal ribs 160 that are guided in longitudinal grooves 154 of driver 150. The latter has an internal spline set 148 that is in engagement with external spline set 146 of tube 41.

FIG. 36 is an exploded view of injection device 30, serving to facilitate comprehension. At the very top is rotary knob 40 with its spline set 125, said knob being fixedly connected to tube 41 as shown in FIG. 20. The latter is equipped with external spline set 146, which serves as part of coupling K2 (FIGS. 25 and 26).

Also depicted in FIG. 36 is driver tube 150 (FIGS. 21 to 24) which has on its outer side 154 three longitudinal grooves 157 (see FIG. 35), only one of which is visible in FIG. 36. By these longitudinal grooves 157, driver tube 150 is coupled nonrotatably, but axially displaceably, to metering element (graduated tube) 66. Metering element (graduated tube) 66 is equipped on its inner side with corresponding longitudinal projections 160 for engagement into longitudinal grooves 157 (see FIGS. 33 and 35).

Piston rod 94 is guided axially displaceably in tube 41 (whose cross-sectional shape is evident from FIG. 18), but, by means of a non-round part 98, it is connected nonrotatably to tube 41 so that a rotation of knob 40 also produces a rotation of piston rod 94, whereas an immobilization of knob 40 immobilizes piston rod 94 in terms of rotation but does not prevent its axial displacement in tube 40.

Internal thread 118 (see FIGS. 15 and 17) of injection sleeve 116 (FIG. 35) is threaded onto metering element (graduated tube) 66 that is equipped with an external thread 72; said sleeve is equipped on its outer side with three longitudinal projections 117 with which injection sleeve 116 is guided in a longitudinal direction in housing part 52. Housing part 52 has for this purpose three longitudinal grooves 53 that are depicted in FIGS. 5, 33, and 35.

Housing part 52 is equipped at its proximal end with external thread 50 which serves for connection to housing part 42, which latter is depicted in FIGS. 3 and 4 but omitted from FIG. 36 for reasons of clarity.

Compression spring 167 is located in rotary knob 40 (see also FIGS. 25 and 26).

Metering element (graduated tube) 66 is latched in a longitudinal direction in housing part 52 (see FIG. 11). Spring 104 interacts with nut 88 (see FIG. 11). Depicted at the very bottom of FIG. 36 is pressure application disk 96 that, after assembly, is installed at lower end 95 of piston rod 94 (see FIG. 30).

It is evident from FIG. 36 that injection device 30 is made up of only a few simple parts that can be assembled very easily and are well suited for automated production. Many variants and modifications are of course possible within the context of the present invention. Normally, for example, the parts of the injection device are manufactured from injection-molded plastic, but highly stressed parts can also be manufactured from metal or from a special plastic, e.g. a plastic with glass-fiber reinforcement. These and other modifications are within the scope of the capabilities of one of ordinary skill in the art.

What is claimed is:

1. An injection device comprising:
   a housing (42, 52) to which a container (34) having injection fluid (32) is connectable;
   a first element (94) for ejecting injection fluid (32) from such a container (34), which first element (94) is shaped with an external thread (92);
   a metering element (66, 88; 166) that is arranged rotatably relative to the housing (42, 52) and has an internal thread (90) that is in engagement with the external thread (92) of the first element (94), which metering element (66, 88; 166) is rotatable, together with the first element (94), relative to the housing (42, 52) for preselection of an injection dose; and
   a coupling arrangement which is implemented to block, during an injection operation, a rotation of the first element (94) relative to the housing (52) but to enable a rotation of the metering element (66, 88; 166) relative to the housing (42, 52),
   so that, by means of such a rotation of the metering element (66, 88; 166) during an injection operation, an axial displacement of the first element in a proximal direction, toward the patient, is performed, in order to eject injection fluid (32) from such a container (34).

2. The injection device according to claim 1, in which, during the preselection of an injection dose, the metering element (66, 88; 166), and the first element (94) having an external thread (92), are not rotatable relative to one another.

3. The injection device according to claim 1, in which, during the preselection of an injection dose, the metering element (66, 88; 166) and the first element (94) having an external thread (92) are rotatable together relative to the housing (52).

4. The injection device according to claim 1, in which, during an injection operation, the metering element (66, 88; 166) and the first element (94) having an external thread (92) are rotatable relative to one another.

5. The injection device according to claim 1, in which the metering element (66, 88; 166) that is arranged rotatably relative to the housing (52) is arranged axially nondisplaceably in the housing (52).

6. The injection device according to claim 1, having a coupling arrangement (98, 99) that is coupled axially displaceably, but nonrotatably, to the first element (94).

7. The injection device according to claim 1, having a coupling arrangement (K2) that is implemented to transfer a dose-setting motion to the metering element (66) for preselection of a desired injection dose.

8. The injection device according to claim 1, in which the metering element is implemented as a sleeve (66, 88; 166).

9. The injection device according to claim 1, further comprising a coupling apparatus (K2, 146, 148, 150) that is uncoupled during an injection operation.

10. The injection device according to claim 1, wherein the first element shaped with an external thread (92) is implemented as a plunger (94) that is equipped with an external thread (92).

11. The injection device according to claim 1, wherein a proximal end (95) of the first element (94) is mounted rotatably in a pressure application element (96) which is adapted to perform ejection of injection fluid (32) from a container (34) for such a fluid (32),
    said proximal end (95) of the first element (94) being arranged in a recessed manner in the pressure application element (96).

12. The injection device according to claim 1, wherein the metering element is implemented as a sleeve (66; 166).

13. An injection device comprising
    a housing (52);
    a container (34) for the reception of injection fluid (32), which container (34) is connectable to the housing (52);
    a metering element (66, 88; 166) that is implemented rotatably, but not axially displaceably, relative to the housing (42, 52);
    an external thread (72) associated with the metering element (66, 88; 166);
    a sleeve-shaped element (116) that is implemented axially movably in the housing (52) but not rotatably relative to the housing (52) and has an internal thread (118) that is in engagement with the external thread (72) of the metering element (66, 88; 166), in order to enable, by rotation of the metering element (66, 88; 166) relative to the housing (52), an axial displacement of the sleeve-shaped element (116) within the housing (52) and thereby the setting of an injection dose;
    a manually adjustable dose-setting element (40); and
    a coupling arrangement (122, 125) selectively operable in
    a first mode, forming an engagement between said dose-setting element (40) and said sleeve-shaped element (116) during an injection operation and
    in a second mode, disengaging the dose-setting element (40) from the sleeve-shaped element (116), for preselection of a desired injection dose.

14. The injection device according to claim 13, in which display values (70) indicating an injection dose are provided on the metering element (66, 88; 166).

15. The injection device according to claim 14, in which the display values (70) are arranged in a substantially helical configuration on the metering element (66; 166).

16. The injection device according to claim 13, further comprising
    a first viewing window (54) provided in the housing (52) of the injection device; and
    a second viewing window (130) that is provided in the sleeve-shaped element (116) and is axially displaceable relative to the first viewing window (54), in order to make visible, on the outer side (68) of the metering element (66; 166), through the first viewing window (54) and the second viewing window (130), a display value (70) for the injection dose on the outer side (68) of the metering element (66; 166).

17. The injection device according to claim 16, in which the second viewing window (130) provided in the sleeve-shaped element (116) is dimensioned so that it corresponds substantially to an area occupied by a display value (70) for the injection dose and, with its periphery (134, 136), covers adjacent display values.

18. The injection device according to claim 16, in which the first viewing window (54) provided in the housing (52)

has the shape of an elongated opening whose longitudinal axis extends substantially parallel to a longitudinal direction of the housing (52).

19. The injection device according to claim 16, in which the elongated opening of the first viewing window (54) provided in the housing (52) is dimensioned so that, in the proximal end position of the second viewing window (130), the minimum dose value, and in the distal end position of the second viewing window the maximum dose value, is visible through the relevant viewing windows (54, 130).

20. The injection device according to claim 13, wherein the metering element is implemented as a sleeve (66; 166).

* * * * *